United States Patent
Widdershoven

(10) Patent No.: US 9,435,802 B2
(45) Date of Patent: Sep. 6, 2016

(54) SENSOR, A SENSOR ARRAY, AND A METHOD OF OPERATING A SENSOR

(71) Applicant: NXP B.V., Eindhoven (NL)

(72) Inventor: Franciscus Petrus Widdershoven, Eindhoven (NL)

(73) Assignee: NXP B.V., Eindhoven (NL)

(*) Notice: Subject to any disclaimer, the term of this patent is extended or adjusted under 35 U.S.C. 154(b) by 261 days.

(21) Appl. No.: 13/860,436

(22) Filed: Apr. 10, 2013

(65) Prior Publication Data
US 2014/0128288 A1 May 8, 2014

Related U.S. Application Data

(62) Division of application No. 12/682,608, filed as application No. PCT/IB2008/054102 on Oct. 7, 2008, now abandoned.

(30) Foreign Application Priority Data

Oct. 12, 2007 (EP) ..................................... 07118382

(51) Int. Cl.
*G01N 33/543* (2006.01)
*C12Q 1/68* (2006.01)

(52) U.S. Cl.
CPC ......... *G01N 33/5438* (2013.01); *C12Q 1/6825* (2013.01); *Y10T 436/143333* (2015.01)

(58) Field of Classification Search
CPC ................................................ G01N 33/5438
See application file for complete search history.

(56) References Cited

U.S. PATENT DOCUMENTS

| | | | |
|---|---|---|---|
| 5,721,422 A | 2/1998 | Bird | |
| 6,331,274 B1* | 12/2001 | Ackley | B01L 3/5027 257/E21.43 |
| 6,366,098 B1 | 4/2002 | Froment | |
| 6,833,725 B2 | 12/2004 | Ohkawa et al. | |
| 6,870,373 B2 | 3/2005 | Kollmer et al. | |
| 7,019,305 B2 | 3/2006 | Eversmann et al. | |
| 2001/0014895 A1 | 8/2001 | Sappal | |
| 2002/0012943 A1 | 1/2002 | Fowlkes et al. | |
| 2002/0031294 A1 | 3/2002 | Takeda et al. | |
| 2002/0127733 A1 | 9/2002 | Kovacs | |
| 2002/0158342 A1 | 10/2002 | Tuominen et al. | |
| 2003/0211637 A1* | 11/2003 | Schoeniger et al. | 436/523 |

(Continued)

FOREIGN PATENT DOCUMENTS

| | | |
|---|---|---|
| CN | 1908642 A | 2/2007 |
| WO | 01/14895 A1 | 3/2001 |

(Continued)

OTHER PUBLICATIONS

Duke, T. et al., "Theory of DNA Electrophoresis in Physical Gels and Entangled Polymer Solutions", Physical Review E, vol. 49, No. 3, 10 pgs. (Mar. 1994).

(Continued)

*Primary Examiner* — Melanie Y Brown

(57) ABSTRACT

A sensor device has an arrangement of plural sensors for sensing an analyte which is in at least one of liquid phase or a suspension or a gel. Each sensor includes a nano-electrode and is configured to sense the presence of a particle localized to or bound to the nano-electrode. The sensor is configured to discriminate in real-time the binding of particles to respective nano-electrodes.

19 Claims, 13 Drawing Sheets

(56) References Cited

U.S. PATENT DOCUMENTS

| | | |
|---|---|---|
| 2004/0110277 A1 | 6/2004 | Maeda |
| 2004/0120185 A1 | 6/2004 | Kang et al. |
| 2005/0006234 A1 | 1/2005 | Hassibi |
| 2005/0017190 A1* | 1/2005 | Eversmann ........ G01N 27/4145 250/370.14 |
| 2005/0106758 A1 | 5/2005 | Fukumoto et al. |
| 2005/0168608 A1 | 8/2005 | Fossum |
| 2006/0022693 A1 | 2/2006 | Bazan et al. |
| 2006/0289726 A1 | 12/2006 | Paulus et al. |
| 2008/0060940 A1* | 3/2008 | Hongo et al. ............. 204/403.01 |
| 2008/0073225 A1* | 3/2008 | Paulus .......................... 205/792 |
| 2010/0052080 A1 | 3/2010 | Garcia Tello et al. |
| 2011/0287977 A1* | 11/2011 | Cai et al. ......................... 506/13 |
| 2012/0238473 A1 | 9/2012 | Gridelet et al. |

FOREIGN PATENT DOCUMENTS

| | | |
|---|---|---|
| WO | 2005/106758 A2 | 11/2005 |
| WO | 2008/132656 A2 | 11/2008 |

OTHER PUBLICATIONS

Chen, J.C. et al. "An On-Chip, Interconnect Capacitance Characterization Method with Sub-Femto-Farad Resolution", IEEE Trans. on Semiconductor Manufacturing, vol. 11, No. 2, pp. 204-210 (1998)xx.

Witvrouw, A. et al., "Why CMOS-Integrated Transducers? A Review", Microsystem Technologies-Micro-and Nanosystems-Information Storage and Processing Systems, vol. 6, No. 5, pp. 192-199 (2000).

Berggren, C. et al. "Capacitive Biosensors", Electroanalysis, vol. 13, No. 3, pp. 173180 (2001).

Atkins, P. et al. Atkins' Physical Chemistry—Electrophoresis, pp. 745-747 (2002).

Hofmann F. et al. "Passive DNA Sensor with Gold Electrodes Fabricated in a CMOS Backend Process", Proc. of the 32nd European Solid-State Device Research Conf., pp. 487-490 (2002).

Drummond, T.G. et al. "Electrochemical DNA Sensors", Nature Biotechnology, vol. 21, No. 10, pp. 1192-1199 (2003).

Kerman, K. et al. "Recent Trends in Electrochemical DNA Biosensor Technology", Measurement Science and Technology, vol. 15, pp. R1-R11 (2004).

Bart, M. et al. "On the Response of a Label-Free Interferon-γ Immunosensor Utilizing Electrochemical Impedance Spectroscopy", Biosensors and Bioelectronics 21, pp. 49-59 (2004).

Schienle, M. et al. "A Fully Electronic DNA Sensor With 128 Positions and In-Pixel A/D Conversion", IEEE J. of Solid State Circuits, vol. 39, No. 12, pp. 2438-2445 (2004).

Thewes R. et al. "A CMOS Medium Density DNA Microarray with Electronic Readout", Mater. Soc. Symp. Proc., vol. 869, pp. D3.4. 1-D3.4.11 (2005).

Mabeck, J. et al. "Chemical and Biological Sensors Based on Organic Thin-Film Transistors", Anal Bioanal Chem., vol. 384, No. 2, pp. 343-353 (Jan. 2006).

Veeramachaneni, U. K., et al. "Magnetic Particle Motion in a Gradient Field", Excerpt from the Proc. of the COMSOL Conf., 5 pgs. (2007).

"3.2.3.4 Case study: Biosensors", from "Towards and Beyond 2015: Technology, Devices, Circuits and Systems", Medea+ Scientific Committee, 4 unnumbered introductory pages and pp. 38-42 (Nov. 2007).

Amendment from U.S. Appl. No. 13/420,133 (Jan. 2, 2013).

Wikipedia "Electrophoresis", 4 pgs., retrieved from the Internet http://en.wikipedia.org/wiki/Electrophoresis (Feb. 29, 2012).

Wikipedia "Gel Electrophoresis", 10 pgs. retrieved from the Internet http://en.wikipedia.org/wiki/Gel_electrophoresis (Mar. 14, 2012).

Office Action from U.S. Appl. No. 13/420,133 (Oct. 2, 2012).

Wikipedia "Time-of-Flight Mass Spectrometry", 8 pgs., retrieved from the internet http://en.wikipedia.org/wiki/Time-of-flight_mass_spectrometry (Mar. 14, 2012).

* cited by examiner

| CONVERSION TIME (ms) | OUTPUT DATA RATE (Hz) | -3dB FREQUENCY (Hz) | RMS NOISE (aF/√Hz) | RMS NOISE (aF) | P-P NOISE (aF) | EFFECTIVE RESOLUTION (BITS) | P-P RESOLUTION (BITS) |
|---|---|---|---|---|---|---|---|
| 11.0 | 90.9 | 87.2 | 4.3 | 40.0 | 212.4 | 17.6 | 15.2 |
| 11.9 | 83.8 | 79.0 | 3.1 | 27.3 | 137.7 | 18.2 | 15.9 |
| 20.0 | 50.0 | 43.6 | 1.8 | 12.2 | 82.5 | 19.4 | 16.6 |
| 38.0 | 26.3 | 21.8 | 1.6 | 7.3 | 50.3 | 20.1 | 17.3 |
| 62.0 | 16.1 | 13.8 | 1.5 | 5.4 | 33.7 | 20.5 | 17.9 |
| 77.0 | 13.0 | 10.5 | 1.5 | 4.9 | 28.3 | 20.7 | 18.1 |
| 92.0 | 10.9 | 8.9 | 1.5 | 4.4 | 27.8 | 20.8 | 18.2 |
| 109.6 | 9.1 | 8.0 | 1.5 | 4.2 | 27.3 | 20.9 | 18.2 |

| SIGNAL | DESCRIPTION |
|---|---|
| RPS(m) | ROW PAIR SELECT OF ROW PAIR m |
| CT(2m) | TRANSFER CLOCK OF ROW 2m ($=\Phi_{T,2m}$) |
| CD(2m) | DISCHARGE CLOCK OF ROW 2m ($=\Phi_{D,2m}$) |
| VD(m) | DISCHARGE VOLTAGE OF ROW PAIR m ($=V_{D,m}$) |
| CD(2m+1) | DISCHARGE CLOCK OF ROW 2m+1 ($=\Phi_{D,2m+1}$) |
| CT(2m+1) | TRANSFER CLOCK OF ROW 2m+1 ($=\Phi_{T,2m+1}$) |
| TES | TRANSFER CLOCK FOR EVEN ROW OF SELECTED ROW PAIR |
| TEN | TRANSFER CLOCK FOR EVEN ROWS OF NON-SELECTED ROW PAIRS |
| DES | DISCHARGE CLOCK FOR FOR EVEN ROW OF SELECTED ROW PAIR |
| DEN | DISCHARGE CLOCK FOR FOR EVEN ROWS OF NON-SELECTED ROW PAIRS |
| DVS | DISCHARGE VOLTAGE FOR SELECTED ROW PAIR |
| DVN | DISCHARGE VOLTAGE FOR NON-SELECTED ROW PAIRS |
| DOS | TRANSFER CLOCK FOR ODD ROW OF SELECTED ROW PAIR |
| DON | TRANSFER CLOCK FOR ODD ROWS OF NON-SELECTED ROW PAIRS |
| TOS | DISCHARGE CLOCK FOR ODD ROW OF SELECTED ROW PAIR |
| TON | DISCHARGE CLOCK FOR ODD ROWS OF NON-SELECTED ROW PAIRS |

FIG. 14

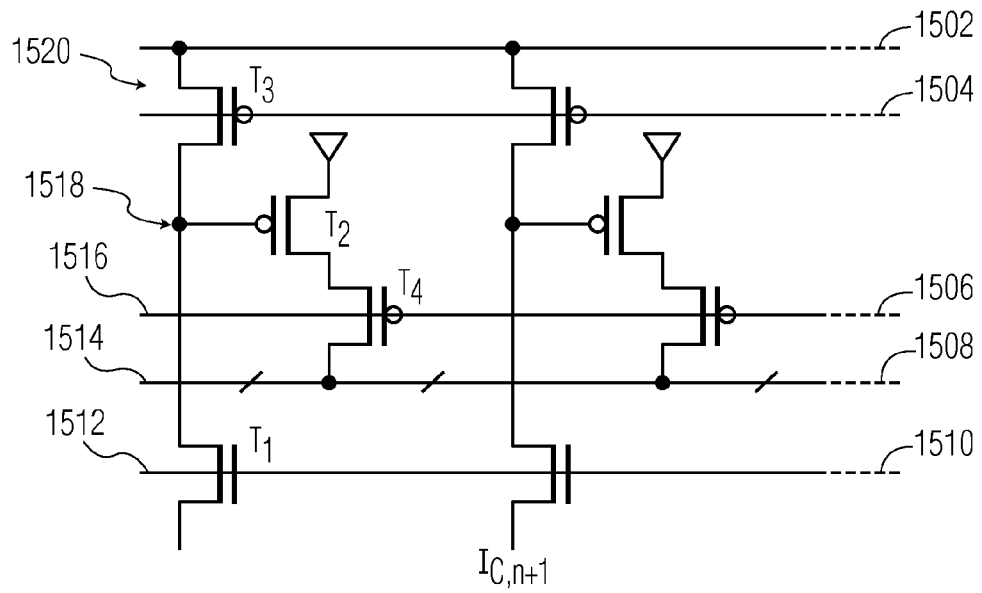

FIG. 15

SENSOR, A SENSOR ARRAY, AND A METHOD OF OPERATING A SENSOR

FIELD OF THE INVENTION

The invention relates to a sensor.
Furthermore, the invention relates to a sensor array.
Moreover, the invention relates to a method of operating a sensor.

BACKGROUND OF THE INVENTION

A biosensor may be denoted as a device which may be used for the detection of an analyte that combines a biological component with a physiochemical or physical detector component.

For instance, a biosensor may be based on the phenomenon that capture molecules immobilized on a surface of a biosensor may selectively hybridize with target molecules in a fluidic sample, for instance when an antibody-binding fragment of an antibody or the sequence of a DNA single strand as a capture molecule fits to a corresponding sequence or structure of a target molecule. When such hybridization or sensor events occur at the sensor surface, this may change the electrical properties of the surface which can be detected as the sensor event.

US 2004/0110277 discloses a bio-sensor comprising a sensor cell matrix in which sensor cells are arranged into a matrix, a row driver which supplies a specific voltage signal to a group of sensor cells lined up in the row direction of the matrix, and a column driver which supplies a specific voltage signal to a group of sensor cells lined up in the column direction of the matrix. Each sensor cell comprises a capacitance element consisting of a pair of opposing electrodes with probe DNA molecules that react selectively with target DNA molecules immobilized to their surfaces, a transistor whose gate terminal is connected to the capacitance element so that the current value that is output from the drain terminal of this transistor is caused to vary in accordance with the amount of the capacitance variation of the capacitance element which is varied by the hybridization of the DNA, and a switching element which supplies a voltage signal supplied from the column driver to the current input terminal of the transistor.

Conventional sensor chips may suffer from a signal to noise ratio which may be too small.

OBJECT AND SUMMARY OF THE INVENTION

It is an object of the invention to provide a sensor having a sufficiently large signal to noise ratio.

In order to achieve the object defined above, a sensor, a sensor array, and a method of operating a sensor according to the independent claims are provided.

According to an exemplary embodiment of the invention, a sensor for detecting particles is provided, the sensor comprising an electrode (which may form one plate of a capacitor), a sensor active region (for instance comprising capture molecules) covering the electrode (for instance being arranged in such a manner that sensor events occurring at the sensor active surface have an impact on the electric condition of the electrode) and being sensitive for the particles, a first switch element operable to bring the electrode to a first electric potential (at a first time) when the first switch element is closed (that is when an electrically conductive coupling between the electrode and a node providing the first electric potential is enabled by the first switch), a second switch element operable to bring the electrode to a second electric potential (at a second time which may differ from the first time) when the second switch element is closed (that is when an electrically conductive coupling between the electrode and a further node providing the second electric potential is enabled by the second switch), and a detector adapted to detect the particles based on a change of the electric properties of the sensor in an operation mode in which the electrode is brought to the first electric potential and an operation mode in which the electrode is brought to the second electric potential (for instance, the amount of the change may be dependent on the presence/absence or the concentration of the particles, since an accumulation of (for instance dielectric) particles in an environment of the sensor active region may change the electric properties, particularly the capacity, of the electrode).

According to another exemplary embodiment of the invention, a sensor array is provided comprising an arrangement of a plurality of sensors having the above-mentioned features. However, multiple sensors may share the same electric potential or sources of electric potential.

According to still another exemplary embodiment of the invention, a method of detecting particles using a sensor is provided, the method comprising bringing a sensor active region covering an electrode in contact with the particles, bringing the electrode to a first electric potential, subsequently bringing the electrode to a second electric potential, and detecting the particles based on a change of the electric properties of the sensor in an operation mode in which the electrode is brought to the first electric potential and an operation mode in which the electrode is brought to the second electric potential.

The term "sensor" may particularly denote any device which may be used for the detection of the presence/absence or even the concentration of particles.

The term "biosensor" may particularly denote any device which may be used for the detection of an analyte comprising biological molecules such as DNA, RNA, proteins, enzymes, cells bacteria, virus, etc. A biosensor may combine a biological component (for instance capture molecules at a sensor active surface capable of detecting molecules) with a physiochemical or physical detector component (for instance a capacitor having a capacitance which is modifiable by a sensor event).

The term "(bio)sensor chip" may particularly denote that a (bio)sensor is formed as an integrated circuit, that is to say as an electronic chip, particularly in semiconductor technology, more particularly in silicon semiconductor technology, still more particularly in CMOS technology. A monolithically integrated biosensor chip has the property of very small dimensions thanks to the use of micro-processing technology, and may therefore have a large spatial resolution and a high signal-to-noise ratio particularly when the dimensions of the biosensor chip or more precisely of components thereof approach or reach the order of magnitude of the dimensions of biomolecules.

The term "biological particles" may particularly denote any particles which play a significant role in biology or in biological or biochemical procedures, such as DNA, RNA, proteins, enzymes, cells, bacteria, virus, etc.

The term "sensor active region" may particularly denote an exposed region of a sensor which may be brought in interaction with a fluidic sample so that a detection event may occur in the sensor active region. In other words, the sensor active region may be the actual sensitive area of a sensor device, in which area processes take place which form the basis of the sensing.

The term "substrate" may denote any suitable material, such as a semiconductor, glass, plastic, etc. According to an exemplary embodiment, the term "substrate" may be used to define generally the elements for layers that underlie and/or overlie a layer or potions of interest. Also, the substrate may be any other base on which a layer is formed, for example a semiconductor wafer such as s silicon wafer or silicon chip. Also a layer sequence may fall under the term substrate as used herein. Such a layer sequence may be formed on and/or in a substrate, that is may be a part thereof.

The term "fluidic sample" or "analyte" may particularly denote any subset of the phases of matter. Such fluids may include liquids, gases, plasma and, to some extent, solids, as well as mixtures thereof. Examples for fluidic samples are DNA-containing fluids, blood, interstitial fluid in subcutaneous tissue, muscle or brain tissue, urine or other body fluids. For instance, the fluidic sample may be a biological substance. Such a substance may comprise proteins, polypeptides, nucleic acids, DNA strands, etc. The analyte may particularly denote a substance that contains the bio-molecules to be analysed (for instance, blood plasma, saliva, urine, food, samples, etc., usually after pre-processing).

The term "capture probe" may particularly denote a molecule that can capture specific target molecules from an analyte.

The term "electrolyte" may particularly denote a substance containing free ions that behaves as an electrically conductive medium (for instance saline water).

The term "electrolytic capacitor" may particularly denote a capacitor comprising or consisting of a metal electrode, coated with an insulating layer (the dielectric), and a electrolyte electrode. The electrolyte can be connected by another metal with a conducting interface to the electrolyte.

The term "redox couple" may particularly denote molecules that can exchange one or more electrons with the electrode surfaces.

The term "SAM" may particularly denote a self-assembled monolayer of organic molecules. A SAM may denote a surface consisting of a single layer of molecules on a substrate. Self assembled monolayers can be prepared simply by adding a solution of the desired molecule onto the substrate surface and washing off the excess.

According to an exemplary embodiment of the invention, a sensor element is provided which has two switch elements adapted for selectively coupling or decoupling an electrode in functional contact with a sensor active portion provided between the two switch elements to one of two different electric potentials (which may be denoted as a transfer potential and a discharge potential). The sensor active region and the electrode may together form a capacitor like configuration (which may be completed by an electrolyte electrode) in which the value of the capacity is dependant on whether a sensor event takes place at the sensor active region or not. Consequently, when first coupling such a sensing capacitor with the first electric potential and afterwards with the second electric potential, a net charge flow during such a procedure may be optionally repeated one or several times may be a characteristic parameter indicative of a sensor element, and therefore indicative of the qualitative or quantitative determination of the particles This of another electric parameter may be detected by a detector (for instance by an amperemeter) and may allow to detect a sensor event with high accuracy, even in a scenario in which only a single biological molecule hybridizes with a corresponding complementary capture probe immobilized on the sensor active region.

Such an architecture may be particularly advantageous when nanoelectrodes are employed which are manufactured sufficiently small. For example, such nanoelectrodes can be made with dimensions of 250 nm, 130 nm or less, and may for instance be realized as sensing pockets having dimensions close to dimensions of biological molecules to the detected. This may allow to obtain a significant improvement of the signal-to-noise ratio. For instance, on a copper nanoelectrode, a self-assembled monolayer (SAM) may be provided which may be specifically designed to attach capture molecules such as antibodies. The copper electrode may then serve, in combination with a second electrode which can be another metallization layer of the semiconductor layer sequence or which can be a counter electrode which may be provided apart from the semiconductor layer sequence, as a capacitor. Sensor events (such as hybridization events between capture molecules immobilized on the SAM layer and target molecules in the sample) may then modify the value of the capacitance of the capacitor.

In the following, further exemplary embodiments of the sensor will be explained. However, these embodiments also apply to the sensor arrangement and to the method.

The electrode may be a sub-micron electrode. In other words, the electrode may have linear dimensions in the order of magnitude of a micrometer or less. Particularly, the electrode can be a nanoelectrode, particularly can have dimensions in a range of essentially one nanometer to essentially some hundred nanometers. By providing electrodes with such a small dimension and consequently with such a small area, the detection sensitivity may be significantly improved, since in such a configuration already few hybridization events or a single hybridization event at the sensor active region may result in a measurable electric signal at the electrode, in a configuration in which the switch elements are operated to electrically couple the electrode alternatingly with the first electric potential and the second electric potential.

The capacitance element may be a single electrode with an area comparable to that of the cross-section of a via (interconnect) plug in an advanced CMOS process. Small physical dimensions may be advantageous for achieving single-molecule resolution. The smaller the electrode size, the higher the relative capacitance change as a result of a single-molecule capture. The footprint area of a captured bio-molecule on the electrode area may determine the corresponding capacitance change. All electrode area that is not covered by the captured molecule may in fact act as a parasitic capacitance in parallel to the capacitance change due to the single-molecule capture. That is why the electrode area should be a small as possible. A specifically appropriate electrode is as small as a molecule, provided the electrode pitch is small enough to ensure a reasonable surface coverage. The detectability of single molecules is a matter of achieving high-enough signal-to-noise ratio. In general, if all dimensions (except the molecule size) scale with the feature size of the CMOS process node (90 nm, 65 nm, 45 nm, etc.), the signal-to-noise ratio (which may be the square of the signal amplitude divided by the variance of the noise) is more or less proportional to the inverse of the sum of the electrode capacitance and its parasitic parallel capacitance. That is why the smallest possible electrodes are appropriate for single-molecule detection. But scaling the electrode size (for instance slightly or much) below the feature size of the CMOS process node does not help anymore because then the sensitivity saturates at a value determined by parasitic, while the surface coverage keeps decreasing.

When the sensor active region comprises a nanoelectrode, the dimensions of the electrode may be in the order of magnitude of nanometers, for instance may be less than 300 nm, for instance may be less than or equal to 250 nm, or may be less than or equal to 130 nm. The smaller the nanoelectrodes, the more sensitive the resulting sensor pocket or planar sensor surface.

The nanoelectrode may comprise copper material, particularly copper material being covered by a self assembled monolayer (SAM). These materials may serve as oxidation protection layers or as barrier layers or for enabling bonding of capture molecules, thereby allowing to implement the relative sensitive material copper which is highly appropriate due to its high electrical conductivity and compliance with procedural requirements. Copper material has chemically similar properties to gold which is conventionally used in biosensing, but which has significant disadvantages because it diffuses rapidly into many materials used in silicon process technology, thereby deteriorating the IC's performance, it is difficult to etch, and gold residues are hard to remove in cleaning procedures. However, less preferred embodiments of the invention may involve gold as well. Furthermore, materials such as aluminium or the like may be used as well, and even gold may be a less preferred example for such a material.

The first switch element and/or the second switch element may be a transistor. Such a transistor may have a gate region and may have two source/drain regions. The gate region of such switch transistors may be coupled to clock signals operating the transistor ins "high" or in a "low" operation mode, thereby selectively rendering the channel region between the two source/drain regions of a respective transistor conductive or not. One of the source/drain regions of a respective one of the two switch transistors is coupled to the respective first or second electric potential, wherein the other two source/drain regions of the two switch transistors are coupled to one another and to the electrode, which may also be denoted as a capacitor plate of the capacitor like sensor region. The transistors may be field effect transistors, bipolar transistors, etc. The transistors may be configured as an N-transistor or a P-transistor, for instance a P-MOS or an N-MOS.

The sensor active region may comprise one or more capture probes adapted for hybridizing with the particles. Such a capture prove may be, for instance, one of the two strands of a DNA helix and may have the property to specifically hybridize only with a particle to be detected having a complementary sequence. Thus, a highly specific sensor active region may be provided which may be based on hybridization events between the capture probes and specific particles.

According to an exemplary embodiment, a clock generator may be provided for providing the first switch element and the second switch element with clock signals to operate the first switch element and the second switch element to alternate between an operation mode in which the first switch element is closed (that is to say is coupled to the first electric potential) and the second switch element is simultaneously opened (that is to say is decoupled from the second electric potential), and an operation mode in which the first switch element is opened (that is to say is decoupled from the first electric potential) and the second switch element is simultaneously closed (that is to say is coupled to the second electric potential). Therefore, the clock signals generated by the clock unit (which may be controlled by or which may be a CPU, central processing unit) allow to operate the two switch elements complementary to one another to enable a non-overlapping sequence of "coupling" and "decoupling" phases. Thus, the clock signals provided with the two gates of the switch transistors may be inverse to one another. This may ensure that, with low effort, a reliable sequence of coupling/decoupling phases of the capacitor sensor with one of the two electric potentials is ensured, and that the pulsed or oscillating switching operation can be repeated several times. By repeating such switching modes, a time average of the detection signal may be obtained which may further allow to improve the accuracy, since artefacts may be filtered out or suppressed by such a repetition.

The detector may be adapted to detect the particles based on a net charge transfer between a node providing the first electric potential and a node providing the second electric potential during one or more cycles in which the electrode is brought to the first electric potential and in which the electrode is brought to the second electric potential As will be explained below (particularly referring to the description of FIG. 1) in more detail, it has been surprisingly found by the present inventors that the net charge transferred in connection with the described switching procedure is an accurate parameter allowing to qualitatively determine the particle concentration.

The sensor may comprise a further electrode configured to be kept at a fixed third electric potential (which may differ from the first electric potential and/or from the second electric potential). This fixed third electric potential may be an electrolyte potential of an electrolyte into which the further electrode is immersed. The constant third electric potential may be maintained by a counter electrode which may also be immersed in an electrolyte. Alternatively, the third electric potential may be maintained by correspondingly controlling electrodes of other sensors of a sensor array, as will be explained below in more detail.

The sensor may be manufactured CMOS technology. A CMOS generation appropriate for manufacturing a specific sensor may be dependent on the size of the electrode to be achieved. For example, for single molecule biosensors, the manufacture of very small electrodes may be favourable, resulting in the selection of an advanced CMOS technology generation. If in another embodiment the provision of larger electrodes is desired to immobilize a larger number of capture probes thereon, a former CMOS technology may be an appropriate choice.

The biosensor device may be monolithically integrated in a semiconductor substrate, particularly comprising one of the group consisting of a group IV semiconductor (such as silicon or germanium), and a group III-group V semiconductor (such as gallium arsenide).

The sensor may be adapted as a biosensor, particular as a single molecule biosensor which is able to detect even the presence of individual or single molecules. The biosensor may be based on a capacitive measurement principle, and may be an electrochemical biosensor.

Next, further exemplary embodiments of the sensor array will be explained. However, these embodiments also apply to the sensor and to the method.

The plurality of (for instance electrically interconnected) sensors constituting the sensor array may be arranged in rows and columns (that is to say in a matrix-like configuration). The rows and columns may be arranged to be aligned perpendicular to one another resulting in a rectangular or matrix-like pattern. Alternatively, it is possible to arrange the sensors in rows and columns forming a hexagonal pattern or the like.

In one embodiment, the first electric potential may be provided in common for at least two, particularly for all sensors of a column and the second electric potential may be provided in common for at least two, particularly for all sensors of a row, or vice versa. By taken this measure of applying a common electric potential (such as an electric voltage) to more than one sensor at the same time, a very efficient control of the entire system is made possible, since the electric potential control effort may be kept small.

The clock signals generated by a clock unit may be provided in common for at least two, particularly for all sensors of a row. This clock signal supply architecture may be advantageous since it allows to implement only a very small number of clock generating units in the sensor array by simultaneously supplying the clock signals to multiple sensors at a time. This may also allow for a proper synchronisation of the clock scheme for different sensors.

Sensors in adjacent rows may be arranged upside down to one another to share one of the group consisting of the first electric potential and the second electric potential. In other words, in a matrix like arrangement of the sensors, sensors of adjacent rows (that is rows which are directly next to one another) may be mapped to one another geometrically by using a horizontal mirror plane. Such a configuration may allow two sensors in adjacent rows and in the same column to share the same terminal for providing one of the first and the second electric potentials, resulting in a very dense and efficient configuration with a small number of control lines.

Sensors in adjacent columns may be arranged alternately left/right oriented to one another to share the first electric potential and/or the second electric potential. In other words, also sensors of adjacent columns may be arranged inverse to one another, wherein a mapping of such sensors can be geometrically obtained by a vertical mirror plane. Even this arrangement may contribute to make the electric signal supply scheme even more efficient.

According to an exemplary embodiment, the sensor array may be monolithically integrated in a substrate. Such a substrate may be a semiconductor substrate or any other substrate. It is also possible that such a substrate is formed by a sequence of layers provided on top of each other.

In such a configuration, the first switch element, the second switch element and the detector of the plurality of sensors may be buried within the substrate, that is may be provided beneath a surface of the substrate, for instance may be arranged in one of the lower lying layers of a layer sequence representing the substrate. In contrast to this, the electrode and the sensor active region of the plurality of sensors may be provided at or close to the surface of the sensor array. Thus, the electrodes may be exposed to a fluidic sample under analysis to enable a functional interaction between the sensor active regions and the particles to be detected. Furthermore, a spatial decoupling of the sensor electrodes and the electronic members located deeply within the substrate may further increase the accuracy, since undesired cross-talk between sensor events and electronic control signals may be suppressed by arranging the corresponding members sufficiently far away from one another without significantly reducing the density of the cell arrangement. For example, at least three layers, particularly at least five layers, more particularly at least eight layers may be located between the buried components and the surface bound components.

Particularly, the sensor array may further comprise a moisture resistant structure at the surface of the sensor array between adjacent ones of the electrodes of the plurality of sensors. By taken this measure, it may be securely prevented that a liquid sample under investigation penetrates into the sensor array which might disturb the electronic components embedded therein. By providing such a moisture resistant structure, for example fluorosilicate glass, the life time of the sensor array may be improved.

The sensor array may comprise a selection unit adapted for selecting one of the rows (at a time) for sensing, wherein the selection unit may be further adapted for disabling all other rows from sensing by opening the first switch element and the second switch element of the all other rows. Therefore, the non active rows may be simply biased to be non active, whereas a single row may be activated at a time.

Alternatively, a selection unit may be provided which is adapted for selecting one of the rows for sensing, but is further adapted for disabling all other rows from sensing and for closing the second switch element of at least a part of the all other rows to provide a counter electrode functionality. Only the discharge switch may be closed to include the corresponding electrodes in the reconfigurable counter electrode. This is not possible with the transfer switch because then the corresponding electrode would be connected in parallel with the active sensors element in the same row. In such a configuration, the electrodes which are presently not used for sensing may be not simply made inactive, but may be controlled to serve as a counter electrode to provide the sensor array with a constant electric potential at a position where it is coupled to an electrolyte. Therefore, the presently non-used electrodes may be synergetically used as configurable counter electrode members, which may make a separate counter electrode dispensable and may promote the miniature manufacturability of the sensor array.

The sensor array may further comprise a row periphery circuit comprising a number of multiplexers adapted for gating the rows. Particularly, such a row periphery circuit may comprise five multiplexers for each pairs of rows, the five multiplexers being configured to provide clock signals to operate the first switch element and the second switch element and to provide the first electric potential or the second electric potential to the sensors of a respective pair of rows.

It is noted that the previously described aspect of the invention can be implemented separately from the architecture described in the independent claims, however can be combined with any embodiment described herein. In other words, the previously described aspect is an independent aspect of the invention, which can be implemented without the other provisions disclosed herein. According to such an aspect, a sensor array me be provided comprising an arrangement of a plurality of sensors arranged in rows and columns, the sensor array further comprising a row periphery circuit comprising a number of multiplexers adapted for gating the rows. The row periphery circuit may comprise five (or another appropriate number of) multiplexers for each pair of rows, the five multiplexers being configured to provide clock signals to operate switch elements of the sensors and being configured to provide electric potentials to the sensors of a respective pair of rows.

By such a five multiplexer per row pair architecture, an efficient supply of all control signals and use signals may be ensured, and such a row periphery circuit may be employed with high versatility in different fields, for instance in the field of biosensors or also for controlling an array of memory cells.

The sensor array may comprise a column periphery circuit adapted for gating the columns. Thus, in addition to a row periphery circuit, a column periphery circuit may be implemented to adjust and control the electric potentials supplied to the various columns.

According to an exemplary embodiment, a calibration row may be provided having one or more calibration units each of which being constituted as each of the plurality of sensors but being free of as electrode and a sensor active region. In other words, such a calibration row may have sensors which are only void of the electrode and the sensor active regions. However, all the other components of a sensor may be present in such a calibration unit, so that the measurement of a signal at such a calibration unit may be a proper measure for an unspecific underground signal which is detected by the other sensors as well. Since only the interaction with the particles to be detected lacks for the calibration unit, the use of a calibration row may allow to improve the accuracy of the signals by allowing to calibrate the measured signals on the basis of the underground signal determined by the calibration unit. Alternatively two or more calibration rows may be operated simultaneously to create a larger calibration signal (this may be advantageous to compensate for the effect of the lacking electrodes in the calibration rows). Additionally or alternatively to a calibration row, it is also possible to provide a single calibration cell or a calibration column.

By using an entire row comprising a plurality of calibration units, an average over the individual calibration signals may be calculated to further improve the accuracy of the calibration parameters, since spatially dependent (for instance edge effects) effects can be suppressed by taking such a measure.

The detector of at least a part of the plurality of sensors may be adapted to perform a self referencing function by comparing a detection signal with an average detection signal of at least a part of the other sensors, particularly by comparing the detection signal with an average detection signal of other sensors of a row. For example, time drift effects may be suppressed by taking such a measure, since an individual signal is not considered in an isolated manner, but is compared with a time dependence of an average detection signal of other sensors which may allow to improve the signal to noise ratio and detect even the presence of a single bio-molecule.

The detector may be adapted to detect the particles in an operation mode in which the electrode is statically brought to the first electrical potential and is statically decoupled from the second electrical potential. In such an operation mode, no switching has to take place, so that the clock signals may be maintained at a constant level. In the presence of a time independent signal, it is possible to influence the properties of the capture molecules by such a signal.

The biosensor chip or microfluidic device may be or may be part of a sensor device, a sensor readout device, a lab-on-chip, an electrophoresis device, a sample transport device, a sample mix device, a sample washing device, a sample purification device, a sample amplification device, a sample extraction device or a hybridization analysis device. Particularly, the biosensor or microfluidic device may be implemented in any kind of life science apparatus.

For any method step, any conventional procedure as known from semiconductor technology may be implemented. Forming layers or components may include deposition techniques like CVD (chemical vapour deposition), PECVD (plasma enhanced chemical vapour deposition), ALD (atomic layer deposition), electroplating, or sputtering. Removing layers or components may include etching techniques like wet etching, plasma etching, CMP (chemical mechanical polishing), etc., as well as patterning techniques like optical lithography, UV lithography, electron beam lithography, etc.

Embodiments of the invention are not bound to specific materials, so that many different materials may be used. For conductive structures. it may be possible to use metallization structures, silicide structures, polysilicon structures, or conductive polymer structures. For semiconductor regions or components, crystalline silicon may be used. For insulating portions, silicon oxide or silicon nitride may be used.

The biosensor may be formed on a purely crystalline silicon wafer or on an SOI wafer (Silicon On Insulator).

Any process technologies like CMOS, BIPOLAR, BIC-MOS may be implemented.

The aspects defined above and further aspects of the invention are apparent from the examples of embodiment to be described hereinafter and are explained with reference to these examples of embodiment.

BRIEF DESCRIPTION OF THE DRAWINGS

The invention will be described in more detail hereinafter with reference to examples of embodiment but to which the invention is not limited.

FIG. 14 shows a description of the signals of the row peripheral circuit of FIG. 13 according to an exemplary embodiment of the invention.

FIG. 15 shows a column peripheral circuit according to an exemplary embodiment of the invention.

DESCRIPTION OF EMBODIMENTS

Figure 1:
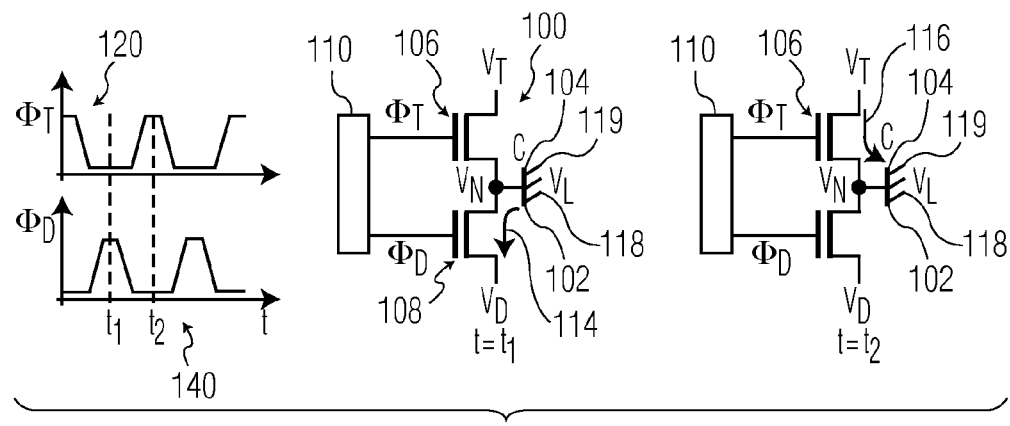
FIG. 1 illustrates a sensor according to an exemplary embodiment of the invention.

The illustration in the drawing is schematic. In different drawings, similar or identical elements are provided with the same reference signs.

In the following, referring to FIG. 1, a biosensor 100 according to an exemplary embodiment of the invention will be explained.

The biosensor 100 is adapted for detecting biological particles (not shown in FIG. 1). The biosensor 100 comprises an electrode 102 as a first capacitor plate of a capacitor denoted with C in FIG. 1. A second capacitor plate is formed by an electrolyte electrode 118 (for instance in a manner similar to FIG. 2). An electrolyte 119 is connected by a separate further electrode (not shown) to connect it to an electrical potential $V_L$.

A sensor active region 104 covers the electrode 102 and is sensitive for the biological particles.

A first field effect switch transistor 106 is provided which is operable to bring the electrode 102 to a first electric potential $V_T$ when the first switch element 106 is closed. In other words, when a clock signal $\Phi_T$ provided by a clock unit 110 is at a "high" level, the channel of the transistor 106 is electrically conductive, so that an electric coupling between the source/drain regions of the first switch transistor 106 is enabled, thereby directly coupling the electrode 102 to the electric potential $V_T$. During the coupling of the electrode 102 to the first electric potential $V_T$, a second clock signal $\Phi_D$ supplied to a gate of a second switch field effect transistor 108 is at a "low" level, so that no electrically conductive coupling is provided between the electrode 102 and a second electric potential $V_D$. In another operation mode, when the second switch element 108 is closed, the electrode 102 is coupled to the potential $V_D$ and is simultaneously decoupled from the potential $V_T$ by applying a "low" signal to the first field effect switch transistor 106 at this time. The complementary clock signals $\Phi_T$ and $\Phi_D$ are shown in diagrams 120, 140.

More particularly, the electrode 102 is coupled to a first source/drain region of the first switch transistor 106 and is coupled to a first source/drain region of the second switch transistor 108. The first electric potential $V_T$ is applied to a second source/drain region of the first switch transistor 106. The second electric potential $V_D$ is applied to a second source/drain region of the second switch transistor 108. The clock signal $\Phi_T$ is applied to a gate of the first switch transistor 106. The clock signal $\Phi_D$ is applied to a gate of the second switch transistor 108.

Hybridization events between the biological particles and the sensor active region 104 may be detected by a detecting unit (not shown in FIG. 1) by determining or measuring a change of the electric properties of the sensor 100 in an operation mode in which the electrode 102 is brought to the first electric potential $V_T$ and an operation mode in which the electrode 102 is brought to the second electric potential $V_D$. A modulation of such a charge transfer may be effected or may be the result of a change of the capacity C in the presence or absence of the particles.

FIG. 1 shows the sensor 100 in an operation mode at a first time t1 at which the clock signal $\Phi_T$ is "low" and the clock signal $\Phi_D$ is "high", so that a coupling between the electrode 102 and the second electric potential $V_D$ is activated, as indicated by an arrow 114, while the electrode 102 is decoupled from the first potential $V_T$. In contrast to this, at a time $t_2$ which is shown in FIG. 1 as well, the clock $\Phi_T$ is "high" and the clock $\Phi_D$ is "low", so that the electrode 102 is coupled to the first electric potential $V_T$, as indicated by an arrow 116, and is decoupled from the second electric potential $V_D$.

By performing the operation cycle shown in FIG. 1 once or several times, a net charge flow may be determined which can be taken as a basis for deriving information regarding the presence or absence and even for the concentration of the particles in an environment of the sensor active region 104. Thus, qualitative or quantitative information about a sample under analysis may be obtained.

Figure 2:
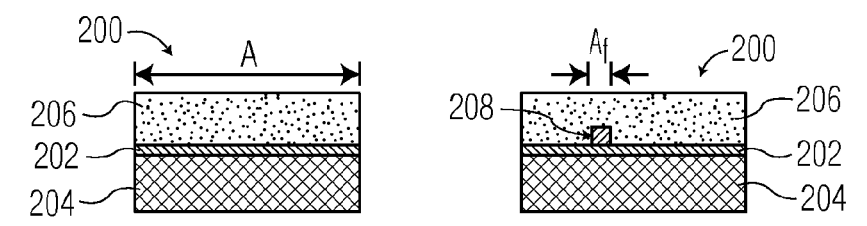
FIG. 2 illustrates a cross-sectional view of a metal-electrolyte capacitor formed by a metal bottom plate, a self-assembled monolayer (SAM) dielectric, and an electrolyte top plate, without (left) and with (right) a bio-molecule captured on the SAM.

Capture probes are immobilized on the electrode 102, forming a part of the sensor active region 104 which may additionally also comprise a self-assembled monolayer (shown and denoted with reference number 202 in FIG. 2).

The clock unit 110 is adapted for providing the first switch element 106 and the second switch element 108 with the clock signals $\Phi_T$ and $\Phi_D$ to operate the first switch element 106 and the second switch element 108 to alternate between an operation mode in which the first switch element 106 is closed and the second switch element 108 is simultaneously opened (t2) and an operation mode in which the first switch element 106 is opened and the second switch element is simultaneously closed (t1).

During this configuration, an electrolyte 119 may be kept at a fixed third electric potential $V_L$ provided by a counter electrode in electrically conductive contact with the electrolyte 119 into which the sensor active surface 104 is immersed.

The electrolytic capacitor C in FIG. 1 is drawn schematically with the following assumptions:

The first electrode 102 is the metal plate;

The dielectric 104 is the sensor active region that is sensitive for biological particles. It is drawn here as an empty space between the first electrode 102 and a second electrode 118;

The second electrode 118 is the interface between the sensor active region 104 and the electrolyte 119. It comprises a self-assembled monolayer (SAM, if present) and the so-called "diffuse double layer" in the electrolyte. The diffuse double layer is the part of the electrolyte immediately above the first electrode and the SAM (if present) where the electric field penetrates. For an electrolyte with physiological salt concentration it has a thickness of the order of magnitude of 1 nanometer. So the actual capacitance of the capacitor C is determined by the series connection of the capacitance of the SAM (if present) and the capacitance of the diffuse double layer.

The electrolyte 119 forms the electrically conducting path between the second electrode 118 and the location (not shown) where the electrical potential $V_L$ is connected.

Next, considerations regarding signal-to-noise ratio will be explained.

FIG. 1 shows an exemplary configuration of the biosensor 100. First, the discharge switch transistor 108 is closed to discharge the "bio-electrolytic" capacitor C to the discharge voltage $V_D$. After a subsequent opening of the discharge switch 108 the charge $Q_D$ on the capacitor C is $$Q_D = (V_D - V_L)(C + C_P) \qquad (1)$$

where $V_L$ is the voltage of the liquid, and $C_P$ is the parasitic capacitance in parallel to the capacitor C. Because of the thermal noise of the series resistance of the discharge switch 108, the charge on the discharged capacitor C fluctuates from one discharged state to another. The variance of these fluctuations, which may be denoted as "reset noise", is $$\sigma_{Q_P}^2 = k_B T(C + C_P) \tag{2}$$

where $k_B$ is Boltzmann's constant, and T is the absolute temperature.

Subsequently the transfer switch transistor 106 is closed to charge the capacitor C to the transfer voltage $V_T$. After subsequent opening of the transfer switch 106 the charge of the capacitor C is $$Q_T = (V_T - V_L)(C + C_P) \tag{3}$$

Because of the thermal noise of the series, resistance of the transfer switch 106, the charge on the charged capacitor C also fluctuates from one charged state to another. The variance of these fluctuations is $$\sigma_{Q_T}^2 = k_B T(C + C_P) \tag{4}$$

The net charge Q transferred from the transfer terminal 106 (at voltage $V_T$) to the discharge terminal 108 (at voltage $V_D$) after N discharge/transfer cycles is $$Q = N(Q_T - Q_D) = N(V_T - V_D)(C + C_P) \tag{5}$$

Because the charge fluctuations of the discharged and charged states are uncorrelated (they originate from different uncorrelated noise sources) the variance of Q is $$\sigma_Q^2 = N(\sigma_{Q_T}^2 + \sigma_{Q_D}^2) = 2Nk_B T(C + C_P) \tag{6}$$

The change in Q as a result of a change $\delta C$ in the capacitor C, caused by the capturing of one or more bio-molecules, is $$\delta Q = N(V_T - V_D)\delta C \tag{7}$$

To be able to detect this capacitance change after N discharge/transfer cycles the signal-to-noise ratio $$\frac{(\delta Q)^2}{\sigma_Q^2} = \frac{N(V_T - V_D)^2 (\delta C)^2}{2k_B T(C + C_P)} \tag{8}$$

should be high enough (the exact number depends on the required detection error probability). In practice additional noise sources of the circuit for measuring Q have to taken into account. There, (8) is an upper limit for the achievable signal-to-noise ratio.

The maximum tolerable modulation voltage $|V_T - V_D|$ is limited by the dielectric reliability properties of C, that is, the leakage current, degradation, dielectric breakdown, etc. of the self-assembled monolayer (SAM). Therefore, for a given SAM and fixed N, the strategy for maximizing the signal-to-noise ratio depends on the use case.

Next, surface coverage fraction measurements will be explained.

For simplicity, the effect of capturing a bio-molecule on top of the SAM is described by the elimination of a small area $A_f$ (the footprint of the captured molecule on the SAM) from the total area A of the capacitor C (see FIG. 2). So the capacitance change associated to a surface coverage fraction $$\gamma = \frac{KA_f}{A} \tag{9}$$

of the SAM by captured bio-molecules is $$\delta C = -\gamma C \tag{10}$$

where K is the number of captured bio-molecules. At fixed $\gamma$ the maximum signal-to-noise ratio $$\frac{(\delta Q)^2}{\sigma_Q^2} = \frac{N(V_T - V_D)^2 \gamma^2 C^2}{2k_B T(C + C_P)} \tag{11}$$

increases with increasing C. So for this use case C and, consequently, its area A, should be as large as possible.

For a properly designed circuit the parasitic capacitor $C_P$ is dominated by the parasitic capacitances of the two switching transistors 106, 108 (mainly junction capacitances and overlap capacitances between the gate electrodes and the source/drain regions). For fixed series resistances of the discharge switch 108 and transfer switch 106 every consecutive CMOS process node (0.35 µm, 0.25 µm, 0.18 µm, etc.) typically has a smaller $C_P$ than its predecessor. But because C has to be large it is not necessary to implement the circuit in a more advanced CMOS generation that required for keeping $C_P$ small compared to C, and for fitting the switching transistors 106, 108 in the are covered by C and its surrounding spaces to isolate it from neighbouring capacitors. Therefore, biosensors 100 for measuring surface covering fractions may be designed in "old" CMOS processes (which may be an attractive opportunity to give old CMOS tabs a second life).

Next single-molecule biosensors will be discussed,

Biosensors that measure surface coverage fractions can be used to measure average properties of ensembles of captured molecules. Furthermore, their large electrodes areas require SAMs with very low defect densities. Single-molecule biosensors may be required to overcome these limitations. They offer the potential to measure properties of individual bio-molecules. Furthermore, because of their small electrode areas, a significant fraction of functional electrodes can be obtained with SAMs with higher defect densities (bad electrodes can be detected and pruned).

The capacitance change associated to capturing a single bio-molecule is given by $$\delta C = -A_f c_0 \tag{12}$$

where the surface capacitance density $$c_0 = \frac{C}{A} \tag{13}$$

of C is a constant, determined by the properties of the dielectric (the SAM) and electrodes (the metal plate and the electrolyte). The associated maximum signal-to-noise ratio $$\frac{(\delta Q)^2}{\sigma_Q^2} = \frac{N(V_T - V_D)^2 A_f^2 c_0^2}{2k_B T(C + C_P)} \tag{14}$$

increases with decreasing C and $C_P$. Therefore, the small feature sizes of advanced CMOS generations offer advantages in realizing the smallest possible values of C and $C_P$.

In a proper design, with nano-electrodes and switching transistors designed using minimum feature sizes, C and $C_P$ typically are of comparable value. Therefore, extending the CMOS process with a dedicated processes option for making sub-feature-size nano-electrodes only has limited advantages because it does not simultaneously reduce the parasitic capacitance $C_P$ and it does not reduce the area occupied by a sensor cell (resulting in a reduction of the fraction of sensitive surface area of the sensor). Therefore, sealing to the next more advanced CMOS generation is the obvious approach for further increasing the signal-to-noise ratio.

Concluding, capacitive biosensors for surface coverage fraction measurement may have large electrodes and can be implemented in old CMOS processes. Single-molecule biosensors may have the smallest possible electrodes and may be implemented in advanced CMOS generations.

In the following, some recognitions of the present inventor will be explained baaed on which exemplary embodiments of the invention have been developed.

Electronic biosensors are attractive because of their potential compatibility with CMOS processes. This allows to integrate the sensor electronics and additional features like an electronic interface to the outside world, programmable functions, and on-chip data storage and processing. In general such sensors consist of one or more electrodes immersed in the analyte. The analyte typically behaves like a liquid electrolyte. Capture probes are attached to the electrode surface, either directly or with some intermediate layer between the electrode surface and the capture probes. Examples of such intermediate layers are SAMs and dielectric layers, or combinations of the two.

Conventionally, sensor electrodes are much larger than the size of the molecules they should detect and/or recognize. However, scaling to nanometer-scaled electrodes may boost the performance of biosensors.

In the following, conventional capacitive bio-sensing will be mentioned.

FIG. 2 is a cross-sectional view of a metal-electrolyte capacitor 200 comprising a metal bottom plate 204, a self-assembled monolayer (SAM) dielectric 202, and an electrolyte top plate 206, without (left) and with (right) a bio-molecule 208 captured on the SAM 202.

The detection principle of a capacitive biosensor may be based on measuring the capacitance of the electrolytic capacitor 200. The surface of the metal electrode 204 is covered with a thin (about 2-nm thick) SAM 202 of organic molecules that serves as a dielectric (FIG. 2, left). The electrode capacitance is $$C = c_0 A \quad (15)$$

where $c_0$ is the capacitance surface density and A is the electrode area. For typical alkane-thiol SAMs with thicknesses about a nanometer the value of $c_0$ is about 0.04 F/m² (the exact number may depend on details of the electrode surface like its roughness on a nanometer-scale, on the composition and density of the SAM, etc.). So for a nano-electrode 204 with an area of 0.015 μm² (a value that should be achievable in a 90-nm CMOS process) C would have a value of about 0.53 fF (1 fF=10⁻¹⁵ F).

The surface of the SAM 202 is chemically functionalised in such a way that it can capture bio-molecules 208. Relevant bio-molecules 208 typically behave as dielectrics with dielectric constants similar to that of the SAM material 202. Their size is in the range of 5 mm to 20 mm. When such a bio-molecule 208 is captured at the surface of the SAM 202 it replaces a certain volume of electrolyte 206. In a simplified picture this event can be modeled as a replacement of a column of conducting electrolyte 206 with footprint area $A_f$ by an insulating dielectric 208 (FIG. 2, right). Assuming that the height of the column is much greater than the thickness of the SAM 202 (because typical bio-molecules 208 of interest are larger than the SAM 202 thickness), and neglecting fringing of the electric field near the intersection of the column wall and the SAM 202, the resulting change in the electrode capacitance is approximately $$\Delta C = -c_0 A_f \quad (16)$$

Assuming that $A_f$ is of the order of magnitude of the square of the bio-molecule 208 size, typical values of |ΔC| can be expected in the range of 1-16 aF (1 aF=10⁻¹⁸ F).

Figure 3:
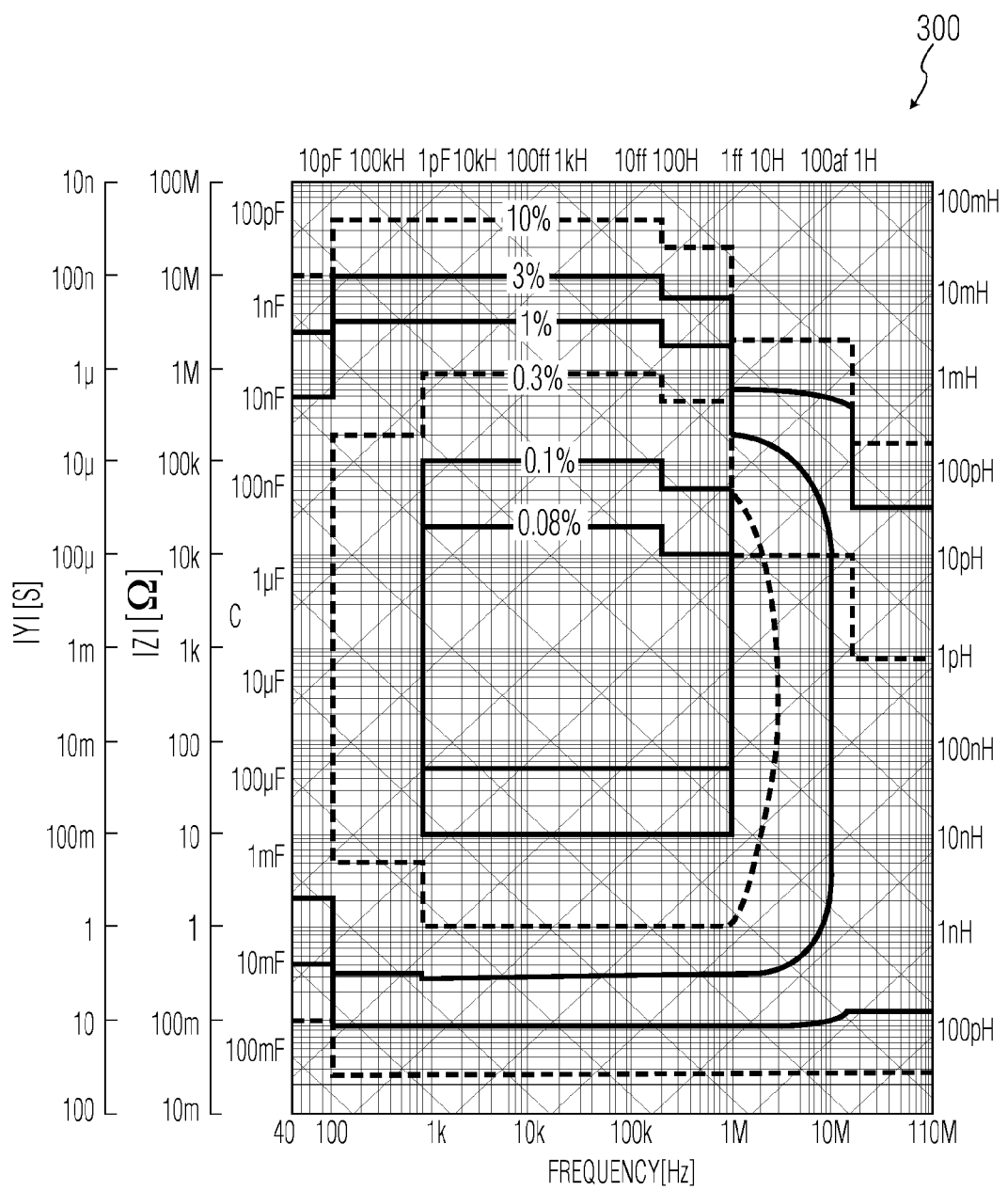
FIG. 3 shows an achievable sensitivity for capacitance measurements with Agilent's Precision Impedance Analyser 4294A being 10 fF at 0.5 Vrms oscillator level (where the 10-fF line touches the 10% accuracy contour line).

Such a small capacitance change is way outside the sensitivity range accessible with off-the-shelf high-end capacitance meters. Even Agilent's Precision Impendance Analyser 4294A can only measure a capacitance of 10 fF with an accuracy of 10% at an oscillator voltage of 0.5 Vrms (see diagram 300 in FIG. 3). But this usually requires long integration times (seconds or more) in a system that has to be carefully screened from interference by external sources. Furthermore, the required accurate calibration for parasitic capacitances may be practically difficult to achieve for a capacitor of which one electrode consists of a liquid (the electrolyte). And the high oscillator voltage may cause unknown nonlinear effects at the electrodes; the long integration times may cause problems with drift, 1/f-noise, etc. But even if one succeeds, the result is just a single capacitance measurement, done with a very expensive system.

Also recently presented high-resolution capacitance meter ICs like the AD7745, AD7746 or AD7747 of Analog Devices cannot measure the typical |ΔC| caused by the capture of a single bio-molecule 208 on the SAM 202 surface. With a conversion time in excess of 100 ms the standard deviation of the capacitance noise is 4.2 aF (see table 400 in FIG. 4, lowest entry in 5$^{th}$ column). Theoretically this would allow measuring a capacitance change of about 10 a F with a reasonable signal-to-noise ration. But this noise figure applies to an excitation (modulation) voltage of $\pm V_{DD}/2$. The exact value of the supply voltage $V_{DD}$ for this particular case is not specified in the IC's datasheet. But the lowest applicable supply voltage of the IC is 2.7 V, so the excitation voltage must be at least 2.7 V top-top, which is much too high for a SAM 202 with a thickness of about 2 nm.

Clearly the capacitance change caused by the capture of a single bio-molecule on the SAM 202 surface is too small for conventional equipment. Therefore the contributions of many molecules have to be added to arrive at a larger capacitance change that can be measured with a sufficient signal-to-noise ration in a reasonable time and at a low-enough modulation voltage (in the 100 mV range). For instance, depending on their size, 630-10,000 bio-molecules have to be captured for a capacitance change of 10 fF, a value which would just be resolvable with a reasonable accuracy with Agilent's 4294A instrument. As a result, even the lowest resolvable capacitance change always will be an average property of a large ensemble of captured bio-molecules. As a result of this averaging process a lot of information about the individual molecules is lost. Especially for a heterogeneous ensemble, consisting of a mix of multiple types of bio-molecules, the measured capacitance change hardly contains any information about the individual types of bio-molecules.

In the following, advantages of massive parallel single-molecule detection will be explained.

Capacitance measurements with electrodes that capture large quantities of bio-molecules give average properties of the captured molecules. As a result, only single-molecule signals common to at least a fraction of the captured ensemble are retained, while all other single-molecule signals are averaged out. In this way the signal-to-noise ration of the common signals can be improved, but all other information about the individual molecules gets lost. Information theoretical considerations show that this is not necessarily the best detection method. For example, variations in the binding details of individual molecules may cause blurring of features in the signals (for instance, inhomogeneous broadening of oxidation/reduction peaks in current-voltage curves, of features in impedance spectra, etc.). If all single-molecule signals could be acquired individually then more reliable detection and/or recognition of bio-molecules would be possible with statistical data processing techniques. Averaging is just one of many possible algorithms that can be applied to the data. But other algorithms can be applied as well (for instance, correction for systematic variations over the ensemble, classification of signals, pruning of bad samples, calculation of correlations, etc.).

An appropriate electronic biosensor can measure all bio-molecules individually. In this way the highest possible amount of information can be extracted from the molecules. For this purpose very small electrodes are needed. They should be placed in a high-density array to achieve high sensitivity (roughly proportional to the fraction of the array area that is sensitive to captured molecules).

The challenge for making biosensors with high-density arrays of individually accessible nano-scale electrodes is the proper segmentation of the addressing, control and read-out electronics into a local part that is repeated in every cell (nano-electrode and local electronics) and a peripheral part that is shared by all cells in a column or row.

Exemplary embodiments of the invention describe an architecture for a high-density capacitive biosensor array that implements such a segmentation in a very efficient way, and that can operate at high speed and very low power consumption. With the disclosed architecture sensors with single-molecule sensitivity can be manufactured.

Apart from an efficient segmentation it may also be important to consider power dissipation. In capacitive biosensor arrays modulation voltages have to be applied to the electrodes or to the counter electrode(s), and the AC currents induced in the electrodes have to be measured. In straight-forward array architectures, where electrodes are selected with selection switches, the AC voltages and/or currents have to be transported through long row and/or column connection lines. This may lead to cross-talk between neighbouring lines or to loss of sensitivity because of large parasitic capacitances of the lines. Furthermore, modulating the voltages of long lines with large parasitic capacitance leads to high dynamic power dissipation. The architecture of embodiments of the invention does not suffer from all these drawbacks, and can be considered optimal in many respects. Furthermore, it can be implemented in standard advanced CMOS processes with only very minor process changes in a very last stage of the processing.

Next, further exemplary embodiments of the invention will be explained.

Embodiments of the invention may implement polished copper nano-electrodes for single-molecule biosensors in advanced CMOS processes. These copper nano-electrodes may serve as sub-micron metal plates of electrolytic capacitors. The dielectrics of the capacitors typical comprise or consist of SAMs, functionalized with capture probe molecules. The electrolyte plates typically comprise or consist of the analyte or a buffer solution above the sensor surface. Capacitors according to this construction are referred hereafter as "nano-electrode electrolytic capacitors".

The above described FIG. 1 shows a configuration of a basic sensor principle according to an embodiment of the invention.

The node voltage $V_N$ of the metal plate 102 of a nano-electrode electrolytic capacitor C is controlled by the two NMOS switch transistors 106, 108, preferably of minimal dimensions (to limit their parasitic capacitances to a minimum). The electrolyte plate 118 of C is maintained at a fixed voltage $V_L$, supplied to the liquid electrolyte 119. The gate voltages of the two switch transistors 106, 108 are controlled by the non-overlapping transfer and discharge clock signals $\Phi_T$ and $\Phi_D$, respectively.

When $\Phi_D$ is "high", the capacitor's metal electrode 102 is discharged to the discharge potential $V_D$ (FIG. 1. t1). After $\Phi_D$ is made "low" again, the transfer clock $\Phi_T$ is made "high". Then the capacitor's metal electrode 102 is charged to the transfer voltage $V_T$ (FIG. 1, t2). Finally, the transfer clock $\Phi_T$ is made "low" again. Assuming that eventual transient peaks in $V_L$ (for instance, as a result of the electrolyte series resistance) have faded out at the end of the switching pulses, the net effect is the transfer of a charge $$Q=(C+C_P)(V_T-V_D) \tag{17}$$

from the transfer terminal (biased at $V_T$) to the discharge terminal (biased at $V_D$), where $C_P$ is the total parasitic capacitance of the $V_N$-node (equation (17) is a special case of equation (5) for N=1). This sequence is repeated with a transfer frequency $f_T$, resulting in an average transfer current $$I_T=f_T Q_T \tag{18}$$

In an array of cells 100, the averaging may be done implicitly by the parasitic capacitance of the column line (the line that connects the transfer terminal, see below). This parasitic capacitance mainly consists of the sum of the parasitic capacitances of the transfer switch transistors of all non-selected cells connected to the same column line. For low frequencies (compared to $f_T/2$) the cell effectively behaves like a resistor $$R_T = \frac{1}{f_T(C+C_P)} \tag{19}$$

The transfer current $I_T$ in principle is independent of the DC-value of electrolyte potential $V_L$. This allows biasing the electrolyte at a convenient potential, for instance, where the average leakage current through the capacitor C is zero, thereby effectively eliminating net long-term electrochemical reactions at the metal/SAM/electrolyte junction.

Next, sensor arrays according to exemplary embodiments of the invention will be explained in more detail.

A single nano-electrode only has a very small area to capture bio-molecules. However, to be able to capture many bio-molecules in a short period of time, a large sensitive area may be needed. Therefore, many cells, each comprising or consisting of a nano-electrode electrolytic capacitor and two switch transistors, may be arranged in a dense two-dimensional array. A high density of cells may be achieved by sharing control, discharge and transfer lines between neighbouring cells in the arrays (control lines are the lines that control the gates of the switch transistors). Because only the part of a cell that is covered by the nano-electrode is sensitive, the fraction of insensitive area of the cell should be made as small as possible. This is another reason to use small switching transistors (apart from reducing their parasitic capacitances).

Figures 4, 5:
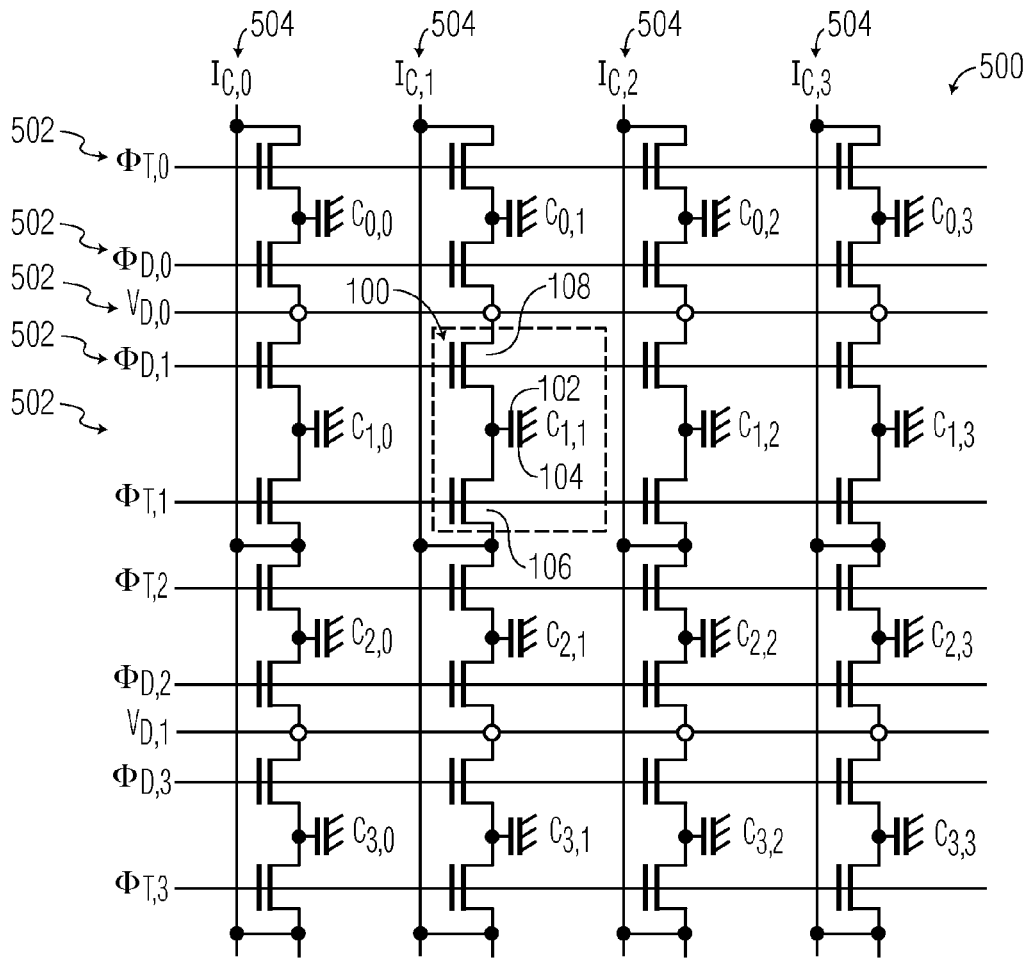
FIG. 4 shows a capacitance input noise and resolution versus conversion time of the Analog Devices "24-bit Capacitance-to-Digital Converter with Temperature Sensor" ICs AD7745 and AD7746.
FIG. 5 shows an array of nano-electrodes and corresponding switch transistors with shared control and discharge lines (horizontal) and transfer lines (vertical) according to an exemplary embodiment of the invention.

FIG. 5 shows an array 500 of nano-electrodes 102 and corresponding switch transistors 106, 108 with shared control and discharge lines (horizontal rows 502) and transfer lines (vertical Columns 504).

In the array architecture of FIG. 5, the cells 100 are arranged in orthogonal rows (each row comprising several control and discharge lines 502; however, in the following, the rows may also be indicated by reference numeral 502) and columns 504. The cells 100 in the odd-numbered rows 502 are oriented upside down with respect to the cells 100 in the even-numbered rows. This allows sharing contact holes and discharge lines in the array layout. All cells 100 in the same row 502 are controlled by the same discharge clock signals $\Phi_{D,m}$ and transfer clock signals $\Phi_{T,m}$, where m is the row index. As a consequence, all nano-electrode 102 electrolytic capacitors in a row 502 are addressed simultaneously. Their transfer currents can be measured via their respective column 504 lines $I_{C,m}$, where n is the column index. With this parallel operation a high detection throughput can be obtained.

Selection of a particular row 502 may proceed by applying the appropriate clock signals and discharge voltage at its control (discharge and transfer clock) and discharge lines. The control lines of the non-selected rows may be biased at alternative appropriate control voltages, for instance, to disable these rows. The entire array or any other subset of rows is scanned by subsequently selecting the respective rows in an appropriate scan sequence.

Next, an advantageous array layout will be explained.

To achieve a high fraction of active sensor array surface it may be advantageous to choose a layout that is as dense as possible. FIG. 6 to FIG. 11 show a dense layout 600, 700, 888, 900, 1000, 1100 that satisfies ail baseline CMOS design rules.

Figure 6:
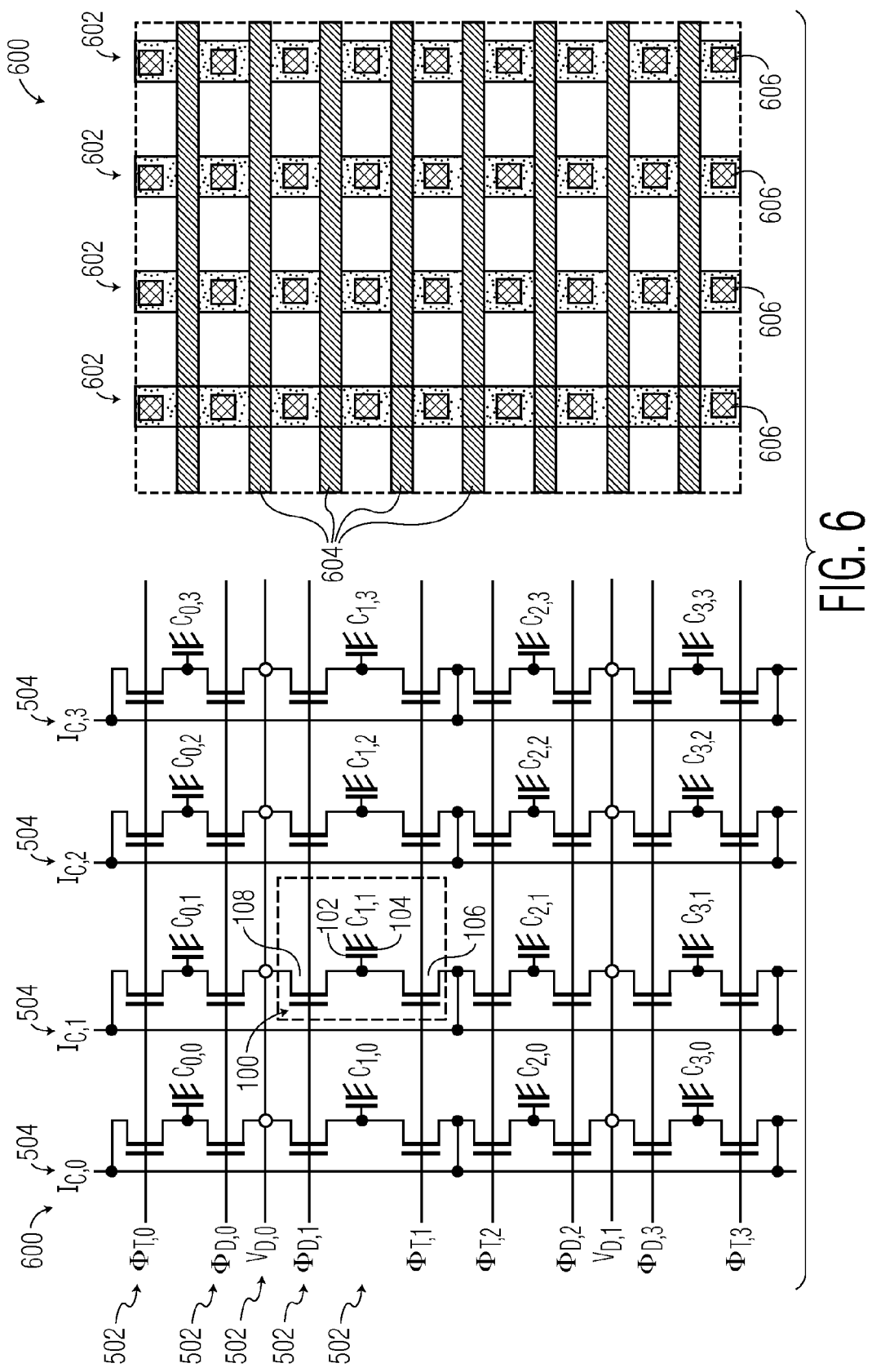
FIG. 6 shows a schematic (left) and layout (right) of the same part of a sensor array according to an exemplary embodiment of the invention.

FIG. 6 shows a schematic (left) and layout (right) portion of the same part of a sensor array. Shown design layers: active 602, poly 604 and contact 606.

Figure 7:
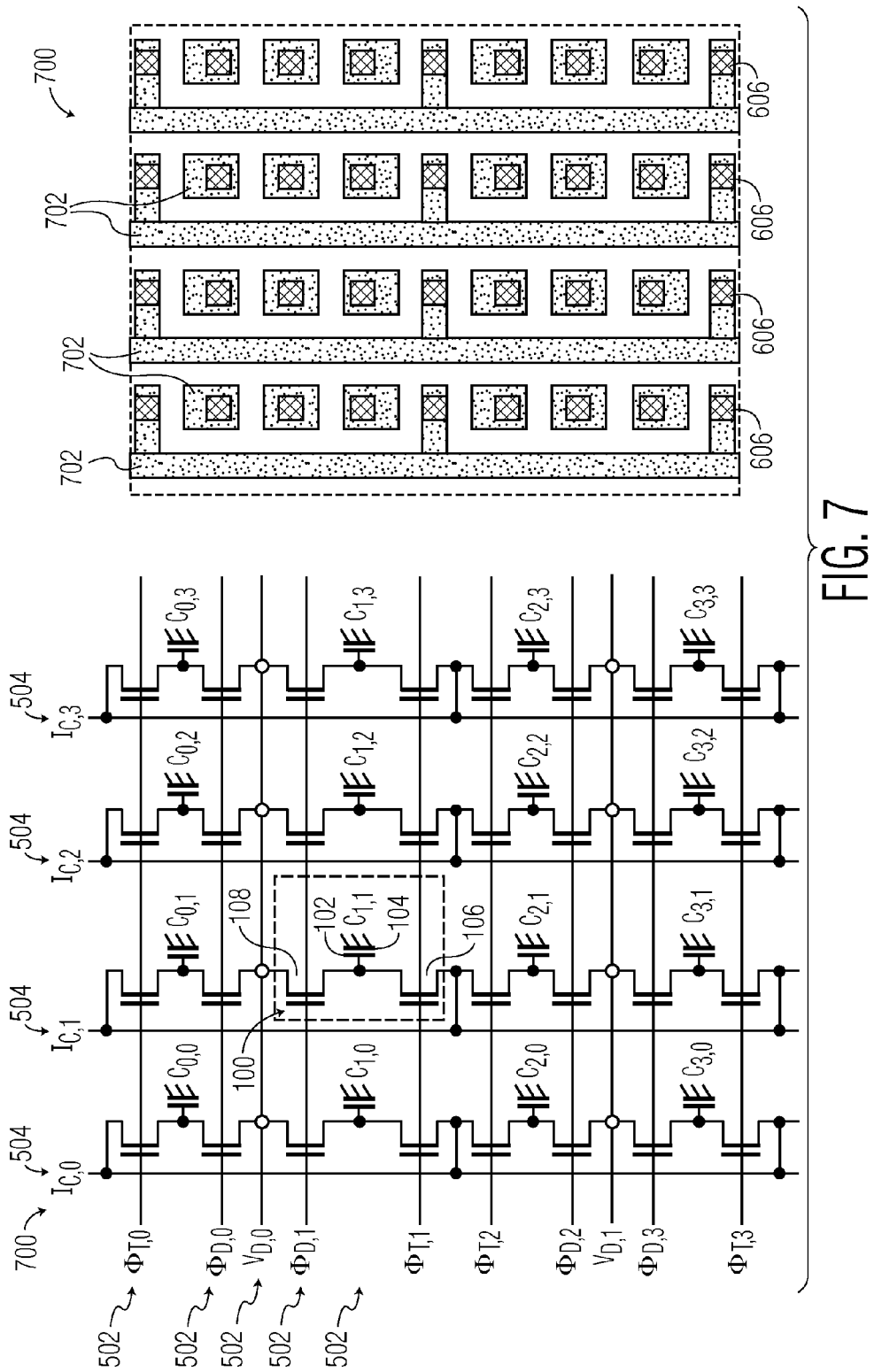
FIG. 7 to FIG. 11 each show a schematic (left) and layout (right) of the same part of a sensor array according to an exemplary embodiment of the invention.

FIG. 7 shows a schematic (let) and layout (right) portion of the same part of a sensor array. Shown design layers: contact 606 and metal-1 702.

Figure 8:
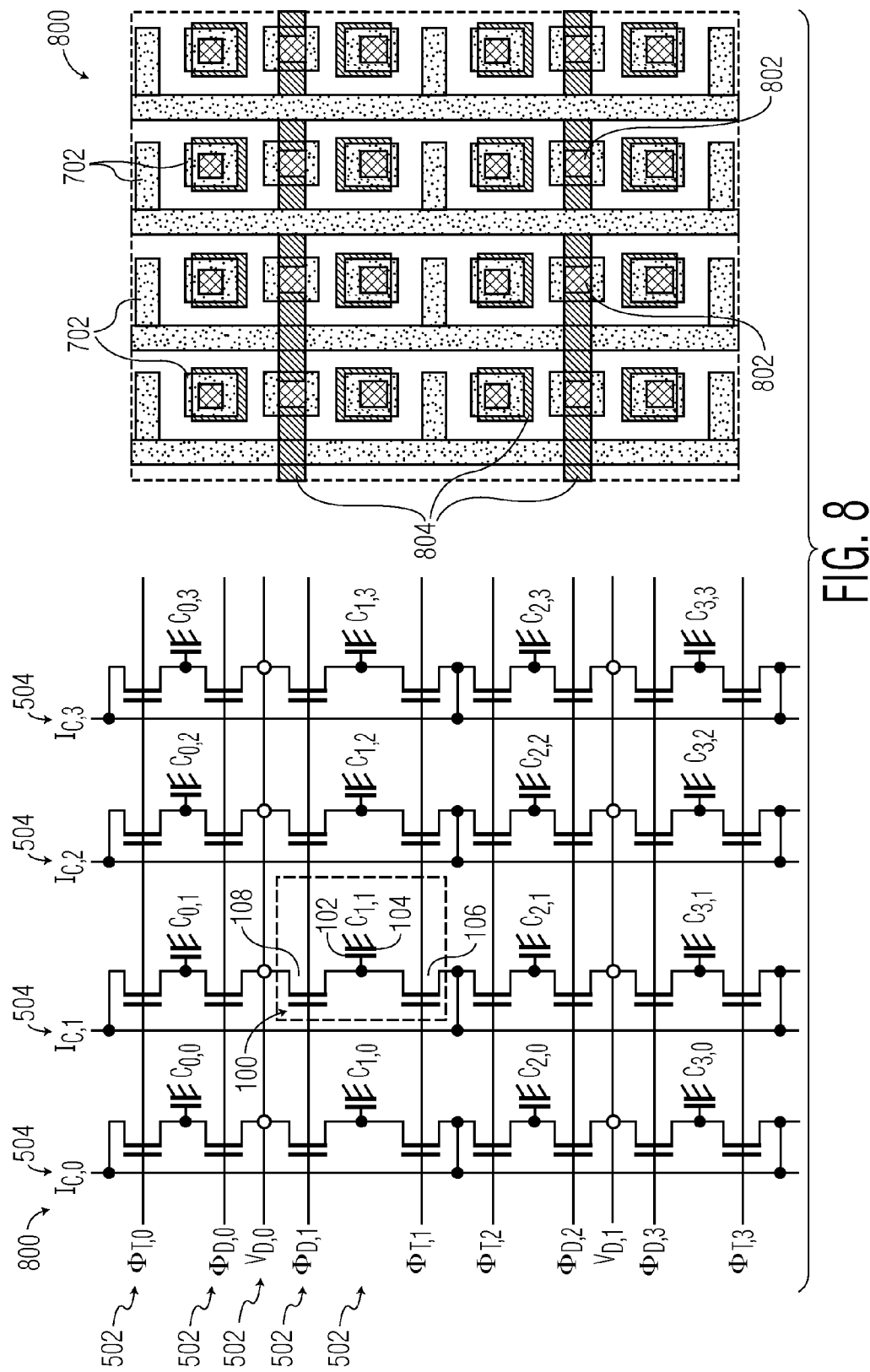

FIG. 8 shows a schematic (left) and layout (right) portion of the same part of a sensor array. Shown design layers: metal-1 702, via-1 802 and metal-2 804.

Figure 9:
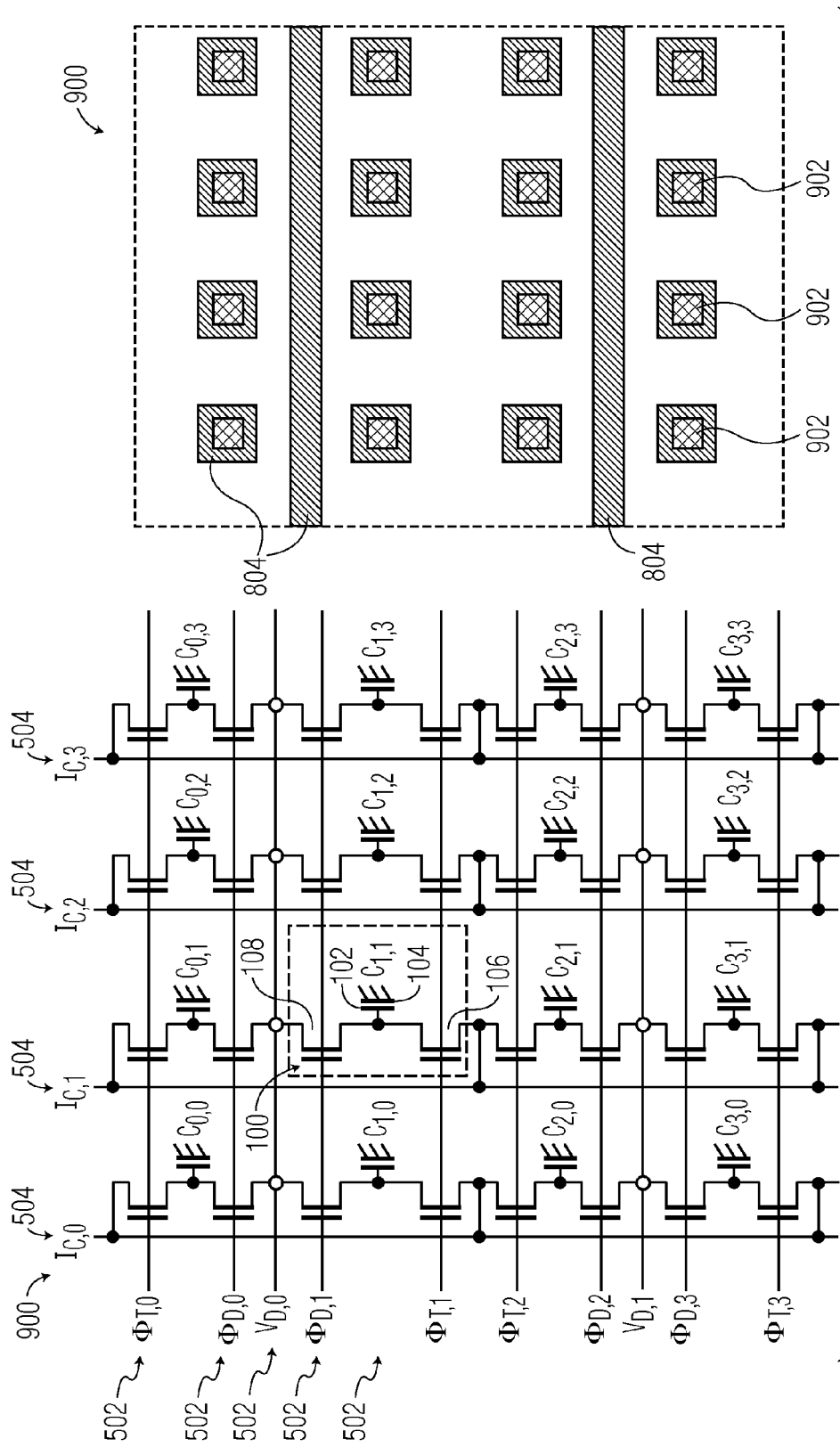

FIG. 9 shows a schematic (left) and layout (right) portion of the same part of a sensor array. Shown: design layers: metal-2 804 and via-2 902.

Figure 10:
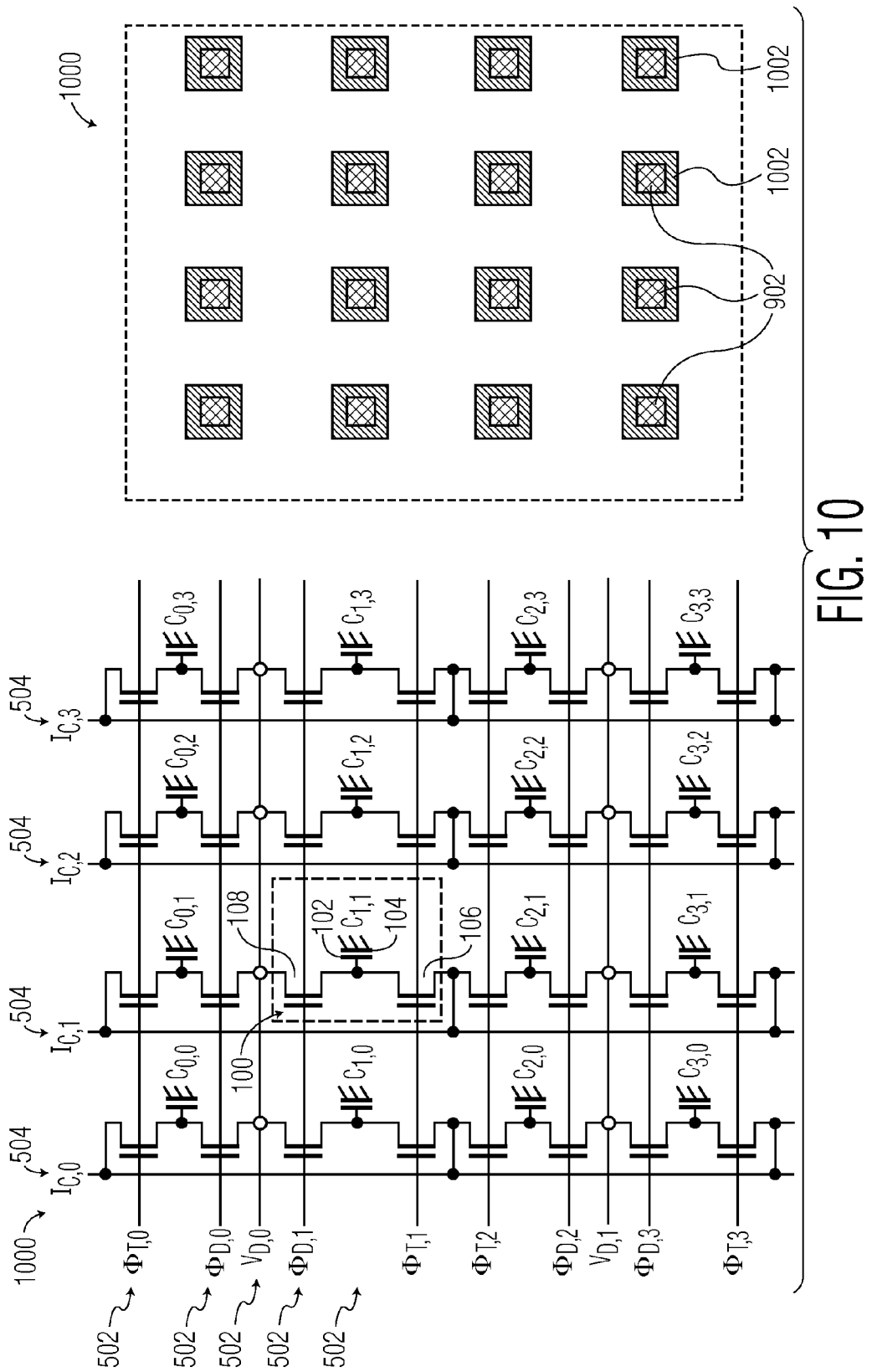

FIG. 10 shows a schematic (left) and layout (right) portion of the same part of a sensor array Shown design layers: via-2 902 and metal-3 1002.

Figure 11:
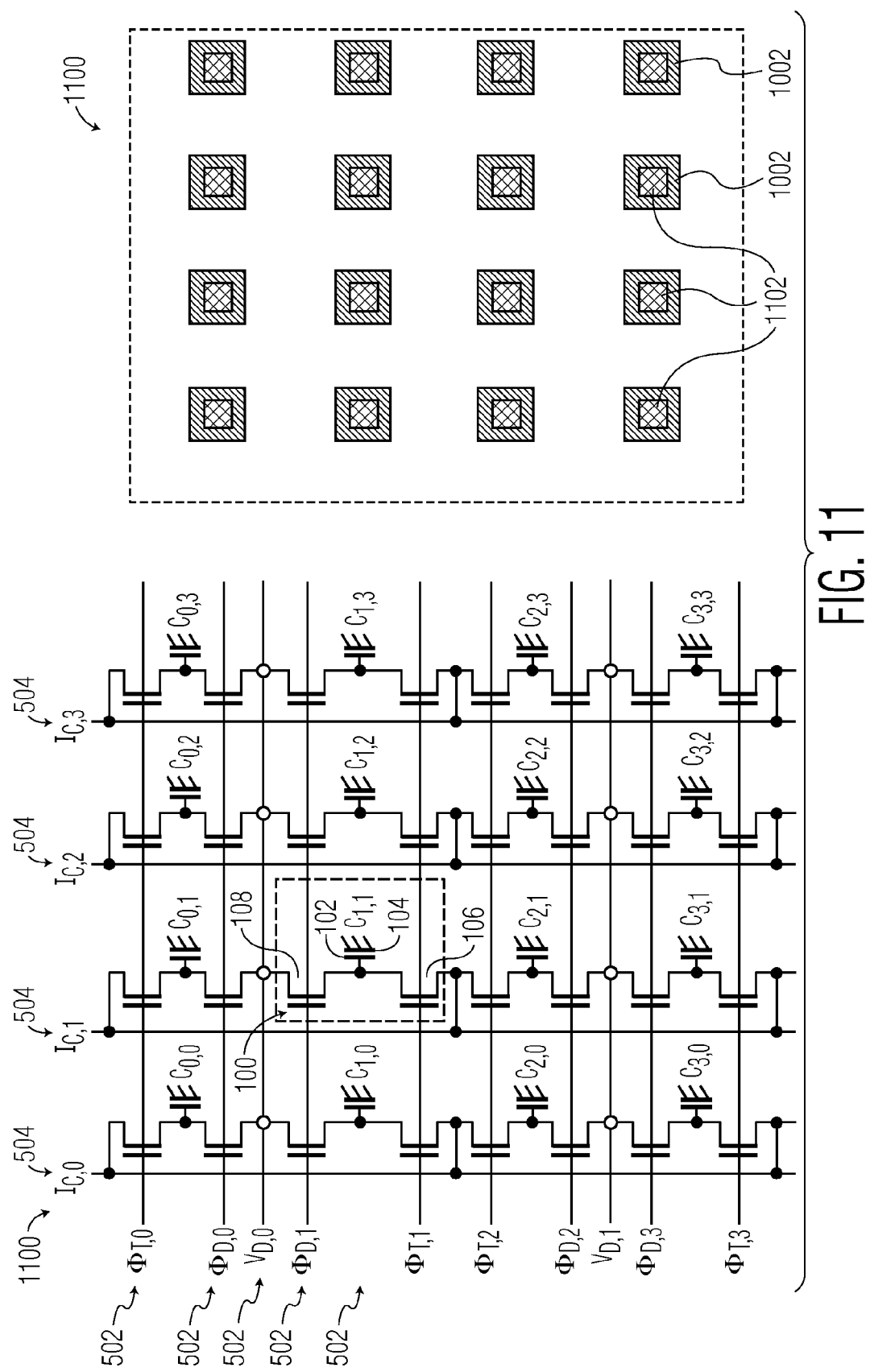

FIG. 11 shows a schematic (left) and layout (right) portion of the same part of a sensor array Shown design layers: metal-3 1002) and via-3 1102 (defining the nano-electrodes).

Active 602 and poly lines 604 are implemented as orthogonal straight lines of minimum possible width (FIG. 6). In the vertical direction the poly line pitch and, consequently, the vertical cell pitch, is limited by the minimum contact-to-poly distance. Minimum-width metal-1 column lines and minimum-area metal-1 landing pads for the connections of the nano-electrodes and the discharge lines determine the horizontal cell pitch (FIG. 7). Discharge lines are implemented in metal-2 804 (FIG. 8). The metal-3 layer 1002 (FIG. 9 to FIG. 11) is included to provide more freedom in the layout of the peripheral and input/output circuits. The via-3 design layer 1102 of the baseline CMOS process is used here to define the nano-electrodes (FIG. 11).

In the following, referring to FIG. 12, a monolithically integrated sensor array 1200 according to an exemplary embodiment of the invention will be explained in more detail.

Figure 12:
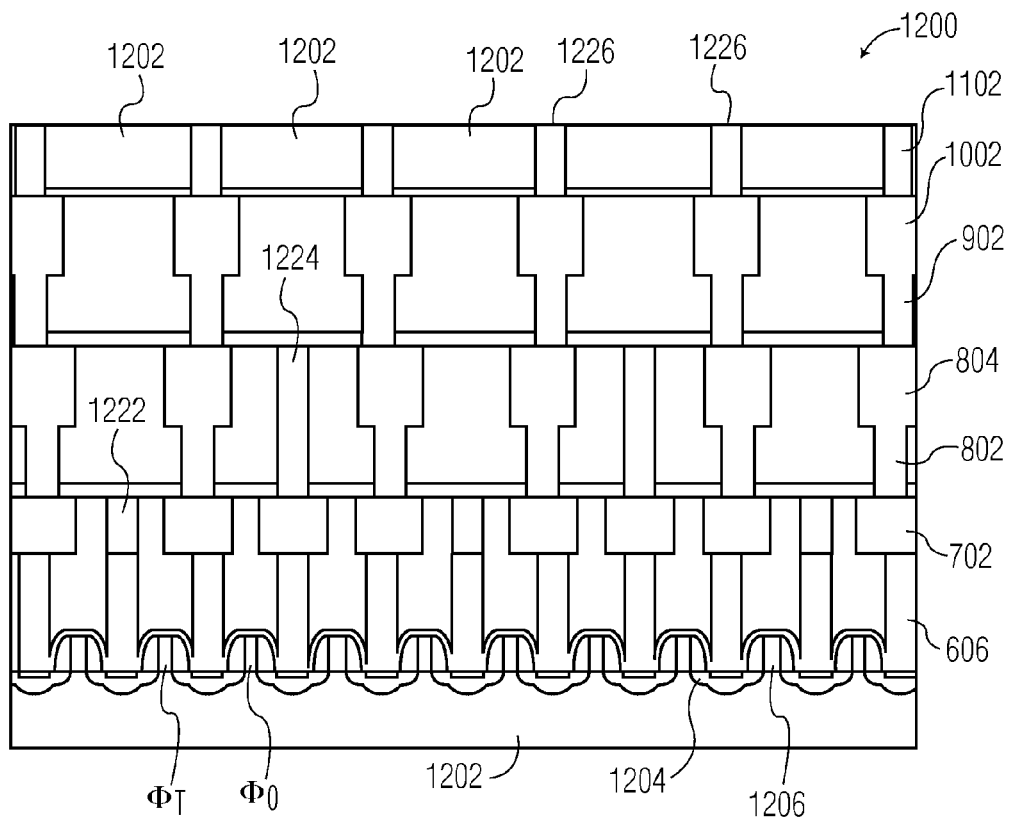
FIG. 12 shows a cross-section along a column through the nano-electrodes of a sensor array according to an exemplary embodiment of the invention.

FIG. 12 shows a cross-sectional view through the sensor array 1200 according to an exemplary embodiment of the invention. FIG. 12 shows a cross-section along a column, through the nano-electrodes.

Up to and including metal-3 1002 the process is identical to the original baseline CMOS process. The top-dielectric 1202 deviates from the low-K dielectric that typically is used at the via-3 level 1102. Instead a moisture-resistance layer 1202, for instance, fluorosilicate glass, is used to prevent penetration of moisture into the layers below. Bond pad access holes (not shown in FIG. 12) are defined in the moisture barrier (at the via-3 level 1102). The via-3 holes and the bond pad access holes are filled simultaneously with a diffusion barrier and copper. A subsequent CMP (chemical mechanical polishing) procedure defines the polished surfaces of the nano-electrodes 1102 and the copper bond pads (not shown).

FIG. 12 shows a p-well 1202 of a silicon substrate. The various switch transistors are shown, more particularly their source/drain regions 1204. Furthermore, a gate 1206 is shown, Contact plugs 606 are shown as well. Furthermore, a first metallization structure 702 can be seen. A first via 802 is indicated as well. A second metal layer 804 is provided above the first via layer 802. A second via layer 902 is provided above the second metal layer 804. A third metallization layer 1002 is provided above the second via layer 902. A third via layer 1102 is provided above the third metallization layer 1002. A column bias strap 1222 to connect the switching transistors to a charge transfer column line is shown as well. Furthermore, row bias lines 1224 (the discharge lines) are indicated. A sense pad 1226 is provided on a surface of the monolithically integrated structure 1200. The surfaces of the via-3 plugs 1102 are the sensitive areas, i.e., the sense pads 1226. Beyond, moisture barriers 1202 are provided between adjacent sense pads 1226.

Alternative embodiments allow creating even smaller cells. For instance, flipping the odd columns 504 around their vertical axis enables sharing the metal-1 landing pads 702 for the discharge line connections of pairs of cells 100 in adjacent odd and even columns 504. This creates some freedom to reduce the horizontal cell pitch by re-optimizing the metal-1 layout 702 without violating the baseline CMOS design rules.

Using self-aligned contacts that overlap with the source/drain sidewall spacers of the switch transistors 106, 108 enables reducing the vertical cell pitch. To avoid violating the metal-1 minimum-area design rule the horizontal cell pitch has to be increased a bit. However, the resulting cell has a less rectangular (more square) shape, which reduces the cell area a bit.

Violating the metal-1 702 minimum-area design rule may be used to reduce the horizontal cell pitch. This can be done, for instance, by fine-tuning the metal-1 702 lithography procedure for a smaller but fixed metal-1 702 landing pad area. Or the regular metal-1 702 landing pads may be replaced by via-like holes, for instance, by means of a double-exposure metal-1 702 litho-step or by other methods known to persons skilled in the art.

Apart from smaller cell sizes other improvements may be considered. For instance, violating the "enclosure of contacts by active" design rule, for instance, by using borderless contacts, may be used to reduce the width of the active lines. Although this does not reduce the cell size, it does reduce the parasitic capacitances between the poly lines and the source/drain junctions of the switching transistors, which in turn increases the dynamic range of the sensor and reduces its dynamic power dissipation.

Using separate discharge lines for odd and even rows may have other benefits, although at the expense of a larger vertical cell pitch. For instance, with separate discharge lines it is not necessary to exclude at least one row form the reconfigurable counter electrode described below.

Instead of via-3 1102 an alternative via level (for instance, a via-4) may be used to implement the nano-electrodes (and the bond pads). In this way more metal levels can be made available for signal or power routing in the array or in the peripheral electronics. Such an approach may be used, for instance, to strap the poly clock lines by metal lines to lower their series resistance.

Of course, combinations of optimizations and improvements may be combined whenever desired.

Next, an array operation and a reconfigurable counter electrode architecture will be explained in more detail.

As an example, the measurement of the capacitances in row 2 will be considered (see FIG. 5). Discharge and transfer clock signals similar to those of FIG. 1 are applied at the control lines $\Phi_{D,2}$ and $\Phi_{T,2}$, and the required discharge voltage is applied at the discharge line $V_{D,1}$. (The index of the discharge lines identifies pairs of rows with shared discharge lines instead of individual rows. So rows $2m$ and $2m+1$ share discharge line m.) In principle all other rows can be disabled by biasing their control lines $\Phi_{D,m}$ and $\Phi_{T,m}$ ($m \neq 2$) at a low potential to switch off their discharge and transfer switch transistors. This requires a separate counter electrode to bias the electrolyte voltage at a voltage $V_L$. In the current context, the counter electrode denotes the electrode that provides the main electrical contact to the electrolyte. Although this is a feasible way of operating the sensor array 500, it involves a couple of challenges.

1. The counter electrode has to be placed external to the sensor chip or it has to be integrated on a separate part of the chip. The first option may make the system more vulnerable for picking up interference signals from external sources like the mains grid, mobile phones, radio stations, etc. The second options may result in a larger chip area (unless the counter electrode can be segmented into pieces that can be distributed over the insensitive surface parts of the cells).

2. If the counter electrode has a different material composition or nano-scale structure than the nano-electrodes, the measured transfer currents may drift as a result of aging of the electrode/electrolyte junctions of the nano- and counter electrodes, and as a result of drift in the temperature, salt concentration or pH of the electrolyte.

3. A sensor system with an external counter electrode may be more complex than one with an integrated counter electrode. For example, it may require at least 1 bond pad to connect the counter electrode, which precludes, for instance, a pure system-on-chip (SOC) sensor system without external parts.

These challenges can be overcome with an alternative biasing scheme for the non-selected rows.

Again, as an example, the selection of row 2 will be considered. Discharge and transfer clock signals similar to those of FIG. 1 are applied at the control lines $\Phi_{D,2}$ and $\Phi_{T,2}$, and the required discharge voltage is applied at the discharge line $V_{D,1}$. As before, all other transfer clock lines $\Phi_{T,m}$ with $m \neq 2$ are biased at a low potential to switch off the corresponding transfer transistors 106. but now all other discharge clock lines $\Phi_{D,m}$ with $m \neq 2$ and $m \neq 3$ are biased at a high potential to switch on the discharge transistors 108 of the corresponding rows 502. This connects their nano-electrodes 102 to their respective discharge lines. In the peripheral of the array 500 (not shown in FIG. 5) these discharge lines $V_{D,k}$ with $k \neq 1$ are all biased at the same reference voltage $V_R$, for instance, by means of addressable pass-gates. In this way the nano-electrodes 102 of all non-selected rows 502, except row 3, effectively are connected in parallel to constitute one large reconfigurable counter electrode with exactly the same composition and nano-scale geometry as that of the selected nano-electrodes 102 in row 2. The nano-electrodes 102 of row 3 have to be excluded from this reconfigurable counter electrode because their discharge line is already biased at the discharge voltage for row 2. Therefore the discharge transistors 108 of row 3 have to switched off by applying a low voltage to the discharge clock line $\Phi_{D,3}$. Such a reconfigurable counter electrode has a couple of advantages over a separate counter electrode:

1. For an array of M rows 502 (m=0, 1, ..., M−1) the effective counter electrode area per selected cell is M−2 times the nano-electrode 102 area. So for large M the contact impedance between the counter electrode and the electrolyte is M−2 times less than that of all selected nano-electrodes 102 in parallel. As a result, the reconfigurable counter electrode effectively controls the electrolyte voltage.

2. After one complete row-scan through the whole array 500 the integrated net charge transport through all nano-electrodes 102 is zero, even if the leakage currents of selected nano-electrodes 102 are not exactly zero (this may happen, for instance, if the reference voltage $V_R$ is not exactly equal to the time average of the voltages of the selected nano-electrodes 102).

3. Because the reconfigurable counter electrode consists of a large amount of nano-electrodes 102 the effects of the captured bio-molecules on the individual nano-electrodes 102 are averaged into an overall effect that compensates for drift caused by the changing average surface composition of the nano-electrodes 102.

Alternative algorithms to group a subset of non-selected nano-electrodes 102 into reconfigurable counter electrodes can be used as well. For instance, only odd-row 502 non-selected nano-electrodes 102 may be used in reconfigurable counter electrodes for odd selected rows 502, and only even-row non-selected nano-electrodes 102 may be used for reconfigurable counter electrodes for even selected rows 502. This approach would effectively split the ensemble of all nano-electrodes 102 into two completely independent sub-ensembles of odd- and even-row 502 nano-electrodes 102, respectively. Such an approach can be advantageous for several reasons (for instance, increased symmetry within each sub-ensemble), but at the expense of an effectively doubled contact impedance between the counter electrode and the electrolyte. Alternatively, only non-selected nano-electrodes 102 of rows 502 in a certain close environment of the selected row 502 may be used. This may be advantageous if external factors cause a gradient in the nano-electrode 102 properties (for instance, during measurements in a flowing electrolyte), but at the expense of an even higher contact impedance between the counter electrode and the electrolyte. Of course, the flexibility in constructing complicated patterns of reconfigurable counter electrodes may be limited by the architecture of the peripheral circuits for the selection of rows 502 and the routing of control- and discharge-line voltages or signals.

Alternatively, in combination with an external counter electrode the reconfigurable counter electrode can also be used as an on-chip reconfigurable reference electrode to monitor the potential of the electrolyte. This effectively turns the reconfigurable counter electrode into a reconfigurable reference electrode with similar properties as that of the currently selected electrodes 102 and, consequently, with similar advantages as a reconfigurable counter electrode (for instance, compensation for drift caused by temporal changes in the composition, temperature, etc. of the electrolyte, or by aging, ware-out, etc. of the SAM layers). The measured electrolyte potential may be exported from the sensor chip, for instance, to control the potential of the external counter electrode.

Next, a row peripheral circuit according to an exemplary embodiment of the invention will be explained.

In the following, row peripheral circuits for arrays with the architecture of FIG. 5 will be described (that is, with shared discharge lines $V_{D,m}$ for even and odd rows $2m$ and $2m+1$). Extension to alternative architectures (for instance, with separate discharge lines for every row) are possible.

The discharge lines $V_{D,m}$ and the discharge and transfer clock signals $\Phi_{D,2m}$, $\Phi_{T,2m}$, $\Phi_{D,2m+1}$ and $\Phi_{T,2m+1}$ of the row pairs m=0, 1, . . . , M/2 (where M is the number of rows) are controlled by a row peripheral circuit. Such a circuit may comprise or consist of an address decoder to select an even/odd row pair, and a signal gating circuit to switch an appropriate discharge voltage and appropriate control signal to the selected row pair. The architecture of a row address decoder may be similar to that for use in memories. Various architectures are possible for signal gating circuits, depending on the required flexibility.

For instance, in an embodiment simple MOS switches may be used to directly connect the discharge line of the selected row pair to a fixed discharge voltage, and all other discharge lines (of the nonselected row pairs) to an alternative voltage or to leave them floating. Simple logic gates may be used to select either the even or the odd row of the selected row pair by applying clock signals to the discharge and transfer clock lines of the chosen row, and to disable the other row of the selected row pair. The other rows of the non-selected row pairs can be either disabled for operation with an external counter or reference electrode or grouped into a reconfigurable counter or reference electrode according to the aimed array operation mode.

Figure 13:
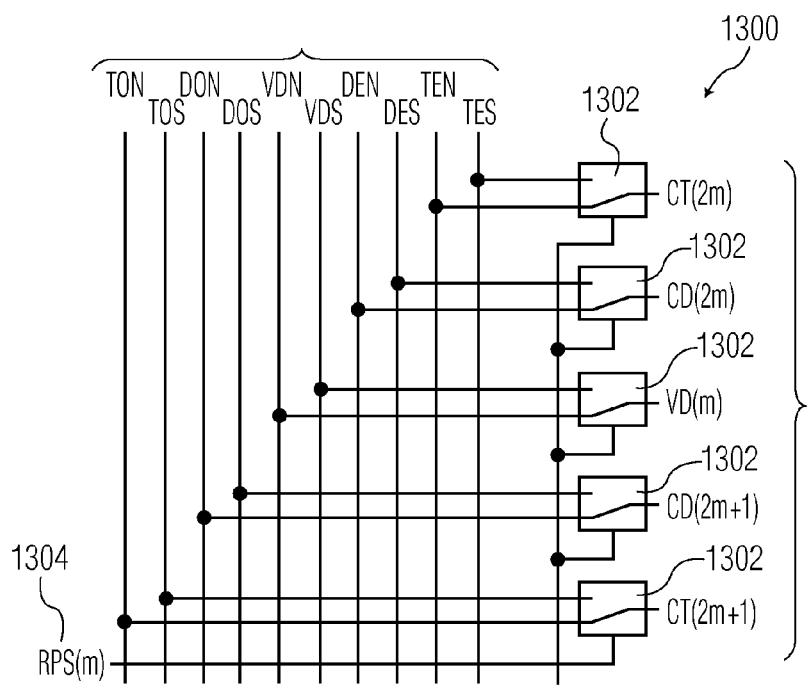
FIG. 13 shows a versatile row peripheral circuit with analog multiplexer switches according to an exemplary embodiment of the invention.

FIG. 13 shows a versatile row peripheral circuit 1300 with analog MUX switches 1302, wherein FIG. 14 shows a table 1400 which describes the signal line. In other words, FIG. 14 is a description of the signals of row peripheral circuit 1300 in FIG. 13.

Thus, FIG. 13 shows an example of a very versatile gating circuit 1300 consisting of five analog multiplexer (MUX) switches 1302 per row pair. The MUX switches 1302 of row pair m are controlled by the row pair select line RPS(m) 1304 originating from a row pair address decoder. The lines CT(2m), CD(2m), VD(m), Cd(2m+1) and CT(2m+1) in FIG. 13 correspond to the lines $\Phi_{T,2m}$, $\Phi_{D,2m}$, $V_{D,m}$, $\Phi_{D,2m+1}$ and $\Phi_{T,2m+1}$ in FIG. 5, respectively. Selecting row pair m puts its five MUX switches 1302 in the upper position while all other MUX switches 1302 (of the nonselected row pairs) remain in the lower position. This allows to apply five independent wave forms to the lines (CT(2m), CD(2m), VD(m), CD(2m+1) and CT(2m+1) via the row control bus lines, TES, DES, VDS, DOS and TOS, respectively, and to apply five alternative independent wave forms to the lines CT(2m′), CD(2m′), VD(m′), CD(2m′+1) and CT(2m′+1) of all non-selected row pairs, where m′=0, 1, . . . , M/2, m′≠m, via the row control bus lines TEN, DEN, VDN, DON and TON, respectively. In this way row $2m$ can be selected by applying appropriate disabling voltages to the lines TOS and DOS. Alternatively, row $2m+1$ can be selected by applying appropriate clock signals to the lines TOS and DOS, while row $2m$ is disabled by applying appropriate disabling voltages to the lines TES and DES. The array can be operated with an external counter or reference electrode by disabling all non-selected rows by putting appropriate disabling voltages on the lines TEN, DEN, VDN, DON and TON. Alternatively, the array can be operated in a reconfigurable counter or reference electrode mode by putting the counter or reference electrode voltage on the line VDN, appropriate enabling voltages on the lines DEN and DON, and appropriate disabling voltages on the lines TEN and TON. The row control bus lines can be connected directly to bond pads. Alternatively, they can be connected to an on-chip wave form generation circuit Next, a column peripheral circuit according to an exemplary embodiment of the invention will be explained.

Typical values of the nano-electrode capacitance C in a 90-nm CMOS process are in the range of 0.5 fF. The parasitic capacitance $C_P$ typically has about the same size as C. The maximum transfer frequency $F_T$ is limited by the series resistance of the poly clock lines of the array and by their distributed load capacitance (mainly the gate capacitances of the switching transistors). As a result, for typical arrays with about 256 columns the maximum value of $f_T$ is about 40 MHz. The maximum amplitude $|V_T-V_D|$ on the measurement node is limited to about 0.2 V by the breakdown and ware-out properties of the SAM and by parasitic electrochemical reactions that make take place at the nano-electrodes. As a result, typical values of the average charge transfer current $I_T$ is of the order of magnitude of 8 nA. This current should be measured with a resolution better than 8 pA to be able to resolve changes $|\delta C|$ down to 1 aF caused by the capture of a single bio-molecule.

Real time monitoring of capturing single bio-molecules on the nano-electrodes requires a temporal resolution of about a second or better, depending on the concentration of the bio-molecules (if the capture event rate is too high the sample may have to be diluted to reduce the concentration). For an array consisting of 256 rows of nano-electrodes this means about 4 ms per row or less, provided that the average charge transfer currents of all columns are measured in parallel. To be able to do this, with a resolution better than 8 pA the measurements may be done on-chip.

FIG. 15 shows a column periphery circuit 1500 having a Reset voltage line 1502, a Reset_not line 1504, a Group select_not line 1506, a Read currents line 1508, a Reference voltage line 1510, voltage clamps 1512, a Read bus 1514, a Read multiplexer 1516, integration caps and read out portion 1518, and Reset MOSTs 1520.

Massive parallel on-chip measurement of the average charge transfer currents can be done in multiple ways. In the embodiment of FIG. 15, the transfer voltage on the column line is controlled by the source follower $T_1$ and the reference voltage line. The drain current of the source follower $T_1$ is integrated on the gate capacitance of transistor $T_2$ after resetting the gate voltage by the reset switch $T_3$. At the end of the integration period the drain of $T_2$ is connected to the read bus by closing the read MUX switch $T_4$. Now the read current (that is, the drain current of $T_2$, which is a measure of the charge integrated on the gate capacitance of $T_2$) can be measured via the corresponding read bus line. Grouping of columns allows multiplexing of read currents over the read bus lines. In that case resetting preferably should also be done per group to arrive at a equal integration period for the groups. The read bus lines can be connected directly to separate bond pads to measure the corresponding read currents with off-chip read electronics. Alternatively, the read bus lines can be connected to on-chip buffer circuits or current-to-voltage converters that export the converted analog signals from the chip via bond pads. Alternatively, the read currents can be digitized by on-chip analog-to-digital converters (ADCs) and exported from the sensor chip via a digital bus.

At an average charge transfer current of 8 nA and an integration time of 4 ms the gate capacitance would have to be equal to 64 pF to limit the voltage swing on the gate capacitance of $T_2$ to about 0.5 V (a typical value for a supply voltage of 1.2 V). This would require a gate are of $T_2$ of about 4500 square microns, which is comparable to the area of a bond pad. This is very large because such a large transistor would be needed for every column. This challenge can be solved by splitting the integration period of 4 ms into multiple smaller integration periods. For instance, for an integration period of 40 microseconds a gate area of 45 square microns is required. However, shorter integration periods correspond to wider signal bandwidth and, consequently, higher noise. Therefore, multiple sequential measurements performed with these shorter integration periods have to be averaged, for instance, on an external computer or with on-chip digital circuits.

In an alternative embodiment of a column periphery circuit the PMOS transistor T2 in FIG. 15 is replaced by a separate integration capacitor and a NMOS source follower transistor. After resetting the voltage on the integration capacitor with the reset transistor T3 the drain current of transistor T1 is integrated on the integration capacitor. The voltage over the integration capacitor is measured by the source follower transistor. The source follower transistor may be selected by the selection transistor T4. Alternatively, the selection transistor T4 may be replaced by a NMOS transistor.

Next, calibration and self-referencing will be mentioned.

Apart from wide-band noise that can be reduced by averaging sequential measurements, the read current may also contain low-frequency noise (often referred to as 1/f-noise) generated by the DC currents flowing through transistors $T_1$, $T_2$ and $T_4$ during the integration period or during the read-out via the read bus (the reset transistor $T_3$ and the discharge and charge transfer transistors of the selected cell do not generate low-frequency noise if the reset, discharge and charge transfer transients are allowed to decay sufficiently at the end of each switching event). This low-frequency noise typically cannot be reduced by averaging subsequent measurements because of its 1/f-like noise power spectral density. Instead, a calibration measurement may be done. For this purpose calibration rows can be used.

Calibration rows may have the same architecture as the active rows, but without nano-electrodes connected to their measurement nodes. As a result, their average charge transfer current is determined only by the parasitic capacitances of their measurement nodes. Because these parasitic capacitances remain constant over time they can be used to generate reproducible reference currents for the columns.

To suppress low-frequency noise, one or more calibration rows may be selected simultaneously, and the total average charge transfer current in every column is measured by means of the column peripheral circuit. Preferably the number of simultaneously selected calibration rows should be chosen in such a way that the total calibration charge transfer current in a column is closest to the charge transfer current of an active row (that is, a row with connected nano-electrodes). Because the nano-electrode capacitance C and the parasitic $C_P$ typically have about similar values, typically two calibration rows have to be measured simultaneously to generate a reference current comparable to the charge transfer current generated by an active cell. If necessary, the reference current can be fine-tuned by means of the charge transfer frequency.

To be able to resolve the small capacitance changes |δC| caused by single-molecule capturing events at the nano-electrodes, the measured capacitances of the individual nano-electrodes can be compared to the average capacitance of a row or set of rows. In this way systematic temporal drift in the nano-electrode capacitances C, for instance, as a result of gradually changing dielectric properties of the SAM layers, can be cancelled (such drift components in general cannot be cancelled by using a reconfigurable counter electrode because the total capacitance of the selected nano-electrodes is much less than that of a typical reconfigurable counter electrode.

In case of a source-follower column periphery circuit the low-frequency noise of source follower transistor can be suppressed further by employing a correlated double sampling strategy. After measuring the voltage on the integration capacitor at the end of the integration cycle the reset transistor T3 is closed to discharge the integration capacitor. While the reset transistor is still closed the voltage on the discharged integration capacitor is measured again (a second time) to serve as a reference for the first measurement. By subtracting the second measurement from the first, the low-frequency noise of the source follower transistor can be eliminated to a large extent. Such a correlated double sampling measurement strategy can be combined with calibration measurements like explained before.

In the following, a system-level architecture according to an exemplary embodiment of the invention will be explained.

Figure 16:
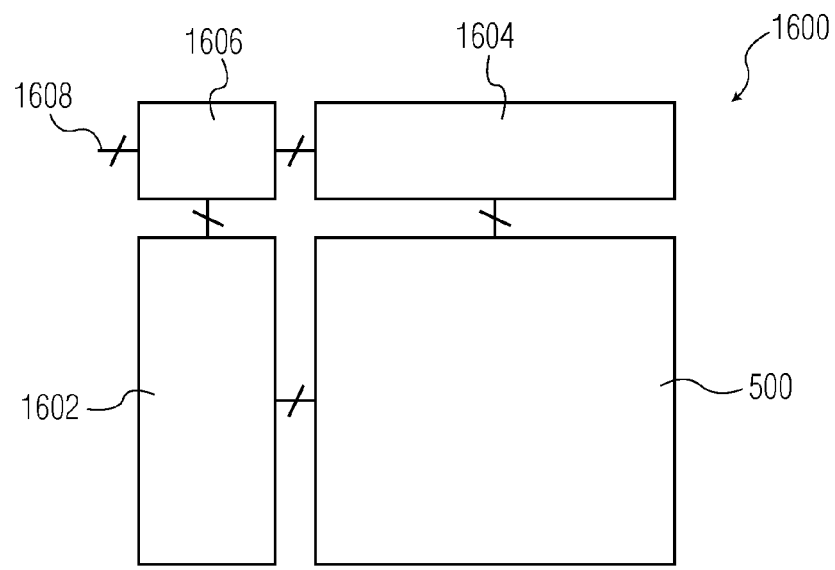
FIG. 16 shows a system architecture according to an exemplary embodiment of the invention.

FIG. 16 shows a system-level architecture 1600 according to an exemplary embodiment of the invention.

The sensor array 500 is controlled by a row peripheral circuit 1602, and the average charge transfer currents of the columns are measured by a column peripheral circuit 1604. The row peripheral circuit 1602 and the column peripheral circuit 1604 connect to a wave form generator (WG) and control block 1606 that is connected to an input-output (IO) bus 1608. The IO bus 1608 inputs the addresses and other control signals and outputs the read currents and other optional output signals. Alternatively, the wave form generator may be off-chip.

Figure 17:
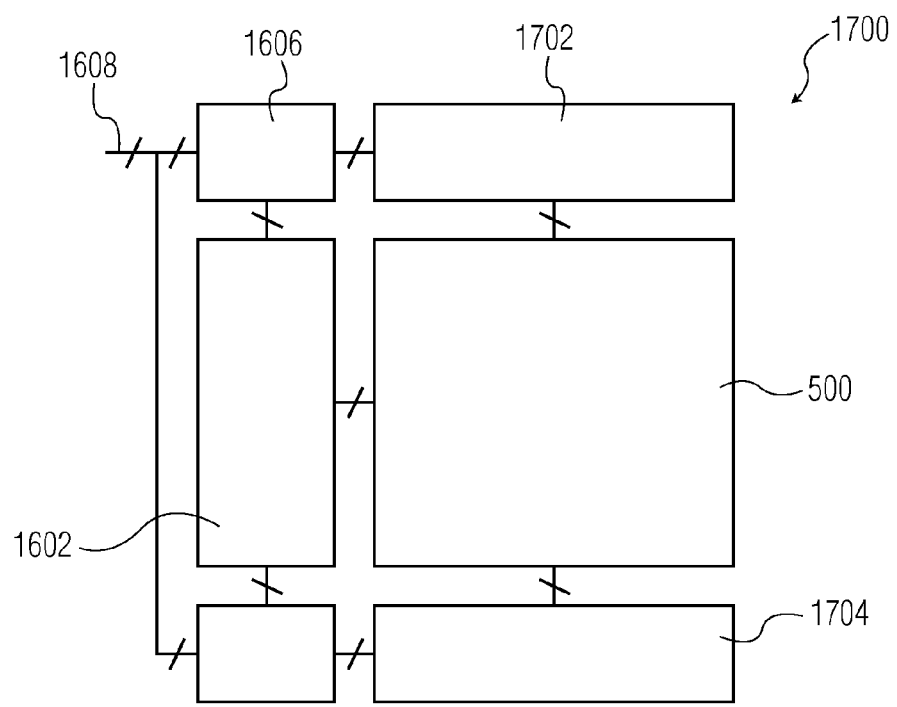
FIG. 17 shows an alternative system architecture according to an exemplary embodiment of the invention.

FIG. 17 shows a system-level sensor-architecture 1700 according to another exemplary embodiment of the invention.

In FIG. 17, separate upper and lower column peripheral circuits 1702, 1704 are provided for even and odd columns, respectively. This architecture may be used to ease the layout of the column peripheral circuit (this may be advantageous because the column pitch typically is smaller that the row pitch).

Figure 18:
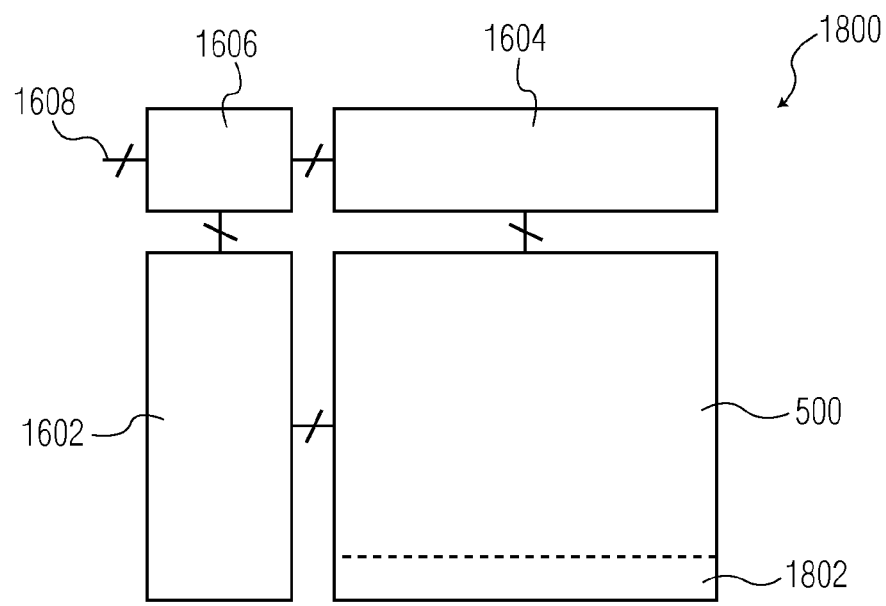
FIG. 18 shows a system architecture of sensor array with calibration rows according to an exemplary embodiment of the invention.

FIG. 18 shows a system-level sensor-architecture 1800 according to still another exemplary embodiment of the invention.

In FIG. 18, calibration rows 1902 are provided which occupy part of the row address space. Additional measures may have to be taken to be able to select more than one calibration row 1802 simultaneously.

Figure 19:
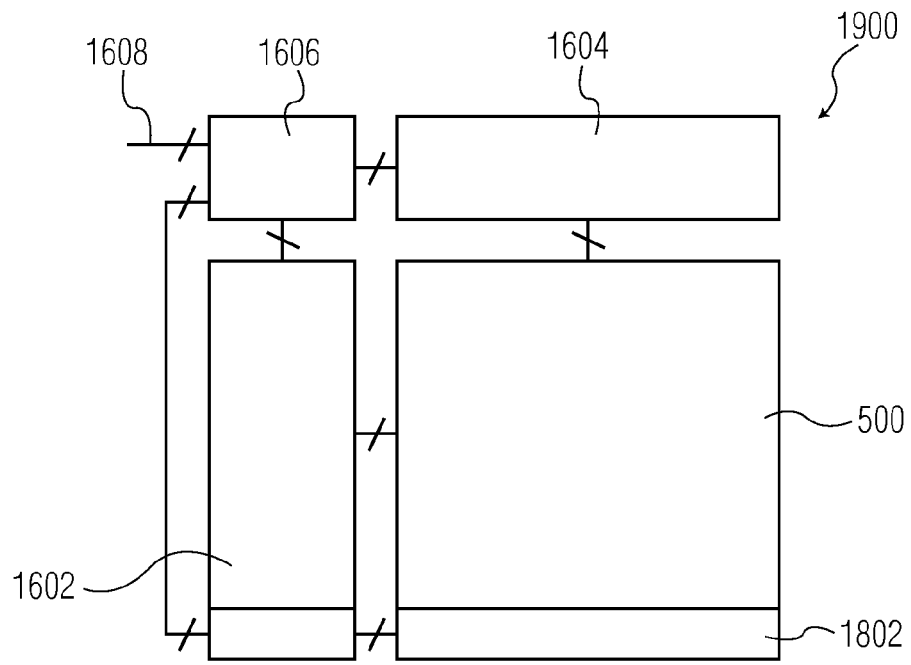
FIG. 19 shows an alternative system architecture of a sensor array with calibration rows according to an exemplary embodiment of the invention.

FIG. 19 shows a system-level sensor-architecture 1900 according to yet another exemplary embodiment of the invention.

In FIG. 19, the calibration rows 1802 are implemented as a separate part of the array that falls outside the row address space 500.

Although embodiments of the invention have been described assuming NMOS switching transistors in the sensor array it is clear that alternative embodiments based on PMOS switch transistors are possible as well.

By sweeping the charge transfer frequency a spectral scan can be made to measure frequency-dependent dielectric properties of individual captured molecules.

Instead of operating the sensor array with clock signals to translate nano-electrode capacitances into charge transfer currents, the sensor may also be used to directly measure DC currents of nano-electrodes by statically disabling the discharge transistors and enabling the charge transfer transistors of the selected row. This may be used to operate the sensor as a massive parallel electrochemical biosensor, for instance to measure DC currents generated by single-molecule enzymes or redox couples captured on the nano-electrodes. Such enzymes or redox couple molecules may be sued as labels to detect bio-molecules.

By statically enabling the discharge transistors and disabling the charge transfer transistors of the selected row, the capturing of molecules on the selected nano-electrodes may be influenced by applying an appropriate voltage on the discharge line of the selected row pair (or row, in case of an architecture with separate discharge lines for every row). During this process the other rows may be used as reconfigurable counter electrodes. By scanning through the rows the capturing of molecules may be influenced on all rows of the sensor. This method may be extended to individual nano-electrodes by applying the required bias voltages via the charge transfer lines instead of the discharge lines. For this purpose the column peripheral circuit may be modified or extended in such a way that difference voltages can be applied to every individual column line. such a way of operation may be used, for instance to enhance the concentration of positively or negatively charged molecules at the selected nano-electrode surfaces to enhance or disable their capturing. For instance, the capturing of negatively charged DNA oligomers (small fragments of DNA) may be influenced this way.

In the following, advantages of exemplary embodiments of the invention will be explained:

Massive parallel single-molecule detection

Extracting maximum possible information from ensemble of captured bio-molecules

Temporal resolution at single-molecule level to measure reaction kinetics

Manufacturability in standard CMOS process with minor BEOL modifications

Using discharge and charge transfer transistor of the same conductivity type (both NMOS and PMOS) allows to make much denser cell layout than using transistors of opposite conductivity type "Natural" scalable; benefiting form Moore's Law Only one plate of the nano-electrode capacitors is connected to the switching elements in the cell. The other plate (the electrolyte) is shared. This enables the extremely compact cell architecture.

Ultra-low power dissipation. In the sensor array dynamic power is only dissipated in the selected row. All non-selected rows only "see" DC voltages (no dynamic power dissipation) and all columns lines only carry very low DC currents.

Virtually no cross talk between adjacent column lines because they effectively only carry DC currents Almost perfect charge balancing possible with reconfigurable counter electrode Reconfigurable counter and reference electrodes have (almost equal composition and history as active electrodes No long signal paths with (on-chip) reconfigurable counter electrodes: minimal pick-up of interference from external sources (radio stations, mains, mobile phones, etc.)

Full CMOS biosensor allows embedding additional functions (A-to-D) converter, microcontroller, memory, etc.) at the lowest price (possibility to design with CMOS library blocks or IP blocks, perhaps modified at the highest metal levels)

Finally, it should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The words "comprising" and "comprises", and the like, do not exclude the presence of elements or steps other than those listed in any claim or the specification as a whole. The singular reference of an element does not exclude the plural reference of such elements and vice-versa. In a device claim enumerating several means, several of these means may be embodied by one and the same item of software or hardware. The mere fact that certain measures are recited in mutually different dependent claims does not indicate that a combination of these measures cannot be used to advantage.

What is claimed is:

1. A sensor device, comprising
an arrangement of a plurality of sensors for sensing an analyte which is in at least one of liquid phase or a suspension or a gel, the plurality of sensors connected by a plurality of row lines and a plurality of column lines, each sensor comprising:
a nano-electrode and being configured to sense a presence of a particle localized to or bound to the nano-electrode,
a first switch circuit configured and arranged to respond to a first row control signal to bring the nano-electrode to a first electric potential by electrically connecting the nano-electrode to a row line of the plurality of row lines; and
a second switch circuit configured and arranged to respond to a second row control signal to bring the nano-electrode to a second electric potential by electrically connecting the nano-electrode to a column line of the plurality of column lines, and
a column periphery circuit that is configured to discriminate in real-time the binding of particles to respective nano-electrodes based on a change of electrical properties of the respective nano-electrodes corresponding with the first electric potential and the second electric potential.

2. A sensor device as claimed in claim 1, wherein the arrangement of a plurality of sensors comprises at least 1000 sensors arranged in an array, and each of the at least 1000 sensors includes:
a capacitor, wherein the nano-electrode is a capacitor plate of the capacitor; and
the first and the second switch circuits include field-effect transistors of a same conductivity type; and
wherein the column periphery circuit is configured to separately sense current flow on each column line of the plurality of column lines.

3. A sensor device as claimed in claim 1, wherein the sensors are arranged in an array on a major surface of the sensor device, each sensor occupying a surface area of no more than 100 µm² of the major surface, wherein the sensors arranged in the array are arranged in rows and columns; and
wherein the first electric potential is provided in common for at least two sensors of a column and the second electric potential is provided in common for at least two sensors of a row, and the first electrical potential discharges voltage stored on sensors by the second electrical potential.

4. A sensor device as claimed in claim 1, configured to discriminate in time between a first group of binding events of particles to respective nano-electrodes and a second group of binding events of particles to respective nano-electrodes, where the first group of binding events and the second group of binding events are separated by more than 1 ms.

5. A sensor device as claimed in claim 4, wherein the first group of binding events and second group of binding events are separated by more than 100 ms.

6. A sensor device as claimed in claim 4, wherein the first group of binding events and second group of binding events are separated by more than 10 s.

7. A sensor device as claimed claim 4, wherein at least one of the first group of binding events and the second group of binding events involves binding no more than 1000 molecules.

8. A sensor device as claimed in claim 4, wherein at least one of the first group of binding events and the second group of binding events involves binding no more than 50 molecules.

9. A sensor device as claimed in claim 4, wherein at least one of the first group of binding events and the second group of binding events involves binding only a single particle.

10. A sensor device as claimed in claim 1, further comprising a biosensor configured for sensing biologically active particles, wherein the first and the second switch circuits are transistors coupled to clock signals operating the transistors in a first and a second operation mode, the first and second operation mode in which the corresponding nano-electrode is discharged and charged to create transfer current, respectively, and wherein the column periphery circuit is further configured to integrate transfer current, during the first operation mode, wherein the first operation mode includes multiple integration periods for which sequential measurements can be performed for each of the integration periods.

11. A sensor device as claimed in claim 10, wherein the nano-electrode includes at least one of a self-assembled monolayer and bio-receptor particle configured to bind a biologically active particle.

12. A sensor device as claimed in claim 10, further comprising a transport structure for transporting a plurality of species of particle to the nano-electrodes from a reservoir, wherein different species of particle take respectively different times to traverse the transport structure from the reservoir to the nano-electrodes.

13. A sensor device as claimed in claim 12, wherein the transport structure is configured such that different species of particle take respectively different times to traverse the transport structure from the reservoir to the nano-electrodes due to one of a group of phenomena comprising elutriation, electrophoresis, magnetophoresis, electromagneto-phoresis, thermophoresis, and chromatography.

14. A sensor device as claimed in claim 1, wherein the arrangement of a plurality of sensors comprises at least 10,000 sensors arranged in an array, wherein the sensors are arranged in rows and columns, the sensor device further including:
a clock generator circuit configured and arranged to provide clock signals to the first and second switch circuits of the plurality of sensors, wherein sensors in a same row are controlled by the same clock signals.

15. A sensor device as claimed in claim 1, wherein the arrangement of a plurality of sensors comprises at least 65,000 sensors arranged in array, wherein the sensors are arranged in rows and columns, the sensor device further including:
a selection unit circuit configured and arranged to select at least one of the rows or columns of sensors or disabling the remaining rows or columns of sensors.

16. The sensor device of claim 1, wherein the nano-electrode is electrically connected to a first source/drain region of the first switch circuit and is electrically connected to a first source/drain region of the second switch circuit and arranged to selectively bring the nano-electrode to the first or second electric potential in response to a clock signal provided to one of the first and the second switch circuits.

17. The sensor device of claim 16, further including clock generator circuitry configured and arranged to provide clock signals to the first and the second switch circuits, wherein a clock signal provided to the first switch circuit is inverse with respect to a clock signal provided to the second switch circuit.

18. The sensor device of claim 1, wherein the first and the second switch circuits are coupled to clock signals and wherein the sensor device further includes:
an arrangement of sensors, the arrangement including the sensor, and
a plurality of multiplexer circuits configured and arranged to provide, responsive to input signals, the clock signals to the first and the second switch circuits.

19. The sensor device of claim 1, wherein the detector circuit is further configured to quantitatively determine particle concentration of the particle in the analyte based on a net charge transfer, a net charge flow determined based on the change of electrical properties of the nano-electrode.

* * * * *